US009552458B2

(12) United States Patent
White et al.

(10) Patent No.: US 9,552,458 B2
(45) Date of Patent: Jan. 24, 2017

(54) COMPREHENSIVE ANALYSIS PIPELINE FOR DISCOVERY OF HUMAN GENETIC VARIATION

(71) Applicant: The Research Institute at Nationwide Children's Hospital, Columbus, OH (US)

(72) Inventors: Peter White, Bexley, OH (US); David Lawrence Newsom, Dublin, OH (US); Yangqiu Hu, Lewis Center, OH (US)

(73) Assignee: THE RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 738 days.

(21) Appl. No.: 13/838,677

(22) Filed: Mar. 15, 2013

(65) Prior Publication Data

US 2013/0311106 A1 Nov. 21, 2013

Related U.S. Application Data

(60) Provisional application No. 61/611,960, filed on Mar. 16, 2012.

(51) Int. Cl.
| | |
|---|---|
| G01N 33/48 | (2006.01) |
| G01N 31/00 | (2006.01) |
| G06G 7/48 | (2006.01) |
| G06G 7/58 | (2006.01) |
| G06F 19/20 | (2011.01) |
| G06F 19/18 | (2011.01) |
| G06F 19/16 | (2011.01) |
| G06F 19/22 | (2011.01) |

(52) U.S. Cl.
CPC ............... *G06F 19/20* (2013.01); *G06F 19/16* (2013.01); *G06F 19/18* (2013.01); *G06F 19/22* (2013.01)

(58) Field of Classification Search
None
See application file for complete search history.

(56) References Cited

PUBLICATIONS

Smith, et al., Identification of Common Molecular Subsequences, Journal of Molecular Biology, Mar. 1981, pp. 195-197, vol. 147, Academic Press Inc. (London) Ltd., United Kingdom.
Li, et al., The Sequence Alignment/Map format and SAMtools, Bioinformatics, May 2009, pp. 2078-2079, vol. 25, No. 16, Oxford University Press, United Kingdom.
(Continued)

*Primary Examiner* — Larry D Riggs, II

(57) ABSTRACT

Systems and methods for analyzing genetic sequence data involve: (a) obtaining, by a computer system, genetic sequencing data pertaining to a subject; (b) splitting the genetic sequencing data into a plurality of segments; (c) processing the genetic sequencing data such that intra-segment reads, read pairs with both mates mapped to the same data set, are saved to a respective plurality of individual binary alignment map (BAM) files corresponding to that respective segment; (d) processing the genetic sequencing data such that inter-segment reads, read pairs with both mates mapped to different segments, are saved into at least a second BAM file; and (e) processing at least the first plurality of BAM files along parallel processing paths. The plurality of segments may correspond to any given number of genomic subregions and may be selected based upon the number of processing cores used in the parallel processing.

60 Claims, 29 Drawing Sheets

(56) References Cited

PUBLICATIONS

Li, et al., Fast and accurate short read alignment with Burrows-Wheeler transform, Bioinformatics, May 2009, pp. 1754-1760, vol. 25, No. 14, Oxford University Press, United Kingdom.

Cock, et al., The Sanger FASTQ file format for sequences with quality scores, and the Solexa/Illumina FASTQ variants, Nucleic Acids Research, Dec. 2009, pp. 1767-1771, vol. 38, No. 6, Oxford University Press, United Kingdom.

Forbes, et al., COSMIC (the Catalogue of Somatic Mutations in Cancer): a resource to investigate acquired mutations in human cancer, Nucleic Acids Research, Nov. 2009, pp. D652-D657, vol. 28, Oxford University Press, United Kingdom.

Collins-Underwood, et al., Genomic profiling of high-risk acute lymphoblastic leukemia, Leukemia (2010), Aug. 2010, pp. 1676-1685, vol. 24, Macmillan Publishers Limited, Germany.

Marin, et al., Assessment of BCR-ABL1 Transcript Levels at 3 Months is the Only Requirement for Predicting Outcome for Patients With Chronic Myeloid Leukemia Treated With Tyrosine Kinase Inhibitors, Journal of Clinical Oncology, Jan. 2012, pp. 232-238, vol. 30, No. 3, American Society of Clinical Oncology, USA.

Depristo, et al., A framework for variation discovery and genotyping using next-generation DNA sequencing data, Nature Genetics, May 2011, pp. 491-498 plus 3 pages, vol. 43, No. 5, Nature Publishing Group, New York City, USA.

Challils, et al., An integrative variant analysis suite for whole exome next-generation sequencing data, BMC Bioinformatics, Jan. 2012, pp. 1471-2105, vol. 13:8, Springer Science+Business Media, Germany.

Lam, et al., Detecting and annotating genetic variations using the HugeSeq pipeline, Nature Biotechnology, Mar. 2012, pp. 226-229, vol. 30, No. 3, Nature Publishing Group, New York City, USA.

McKenna, et al., The Genome Analysis Toolkit: A MapReduce framework for analyzing next-generation DNA sequencing data, Genome Research, Jul. 2010, cover page plus pp. 1297-1303, vol. 20, Cold Spring Harbor Laboratory Press, Woodbury, NY, USA.

Langmead, et al., Searching for SNPs with cloud computing, Genome Biology 2009, Nov. 2009, pp. R134.1-R134.10 (10 pages), vol. 10, Issue 11, Article R134, BioMed Central Ltd., United Kingdom.

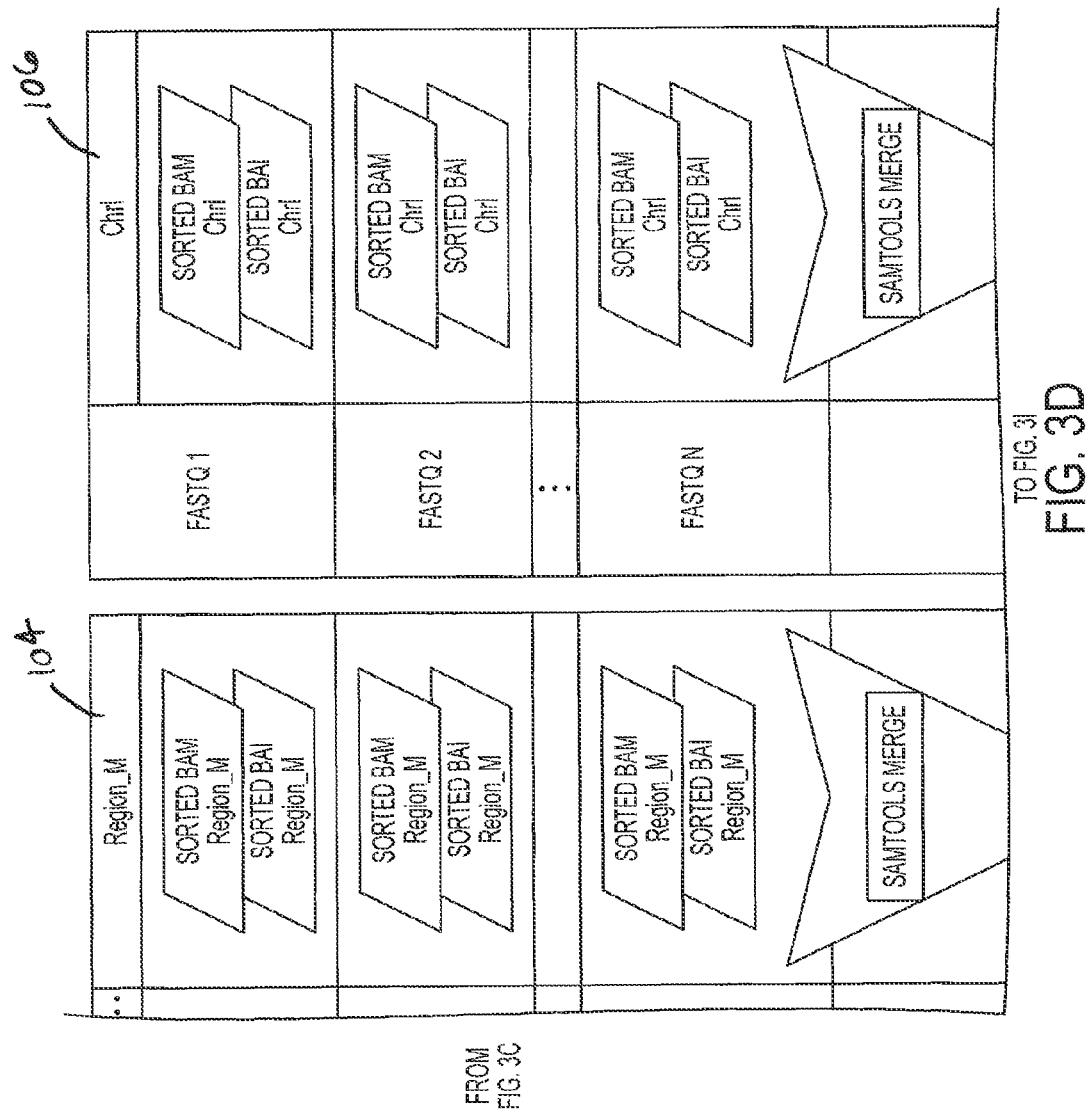

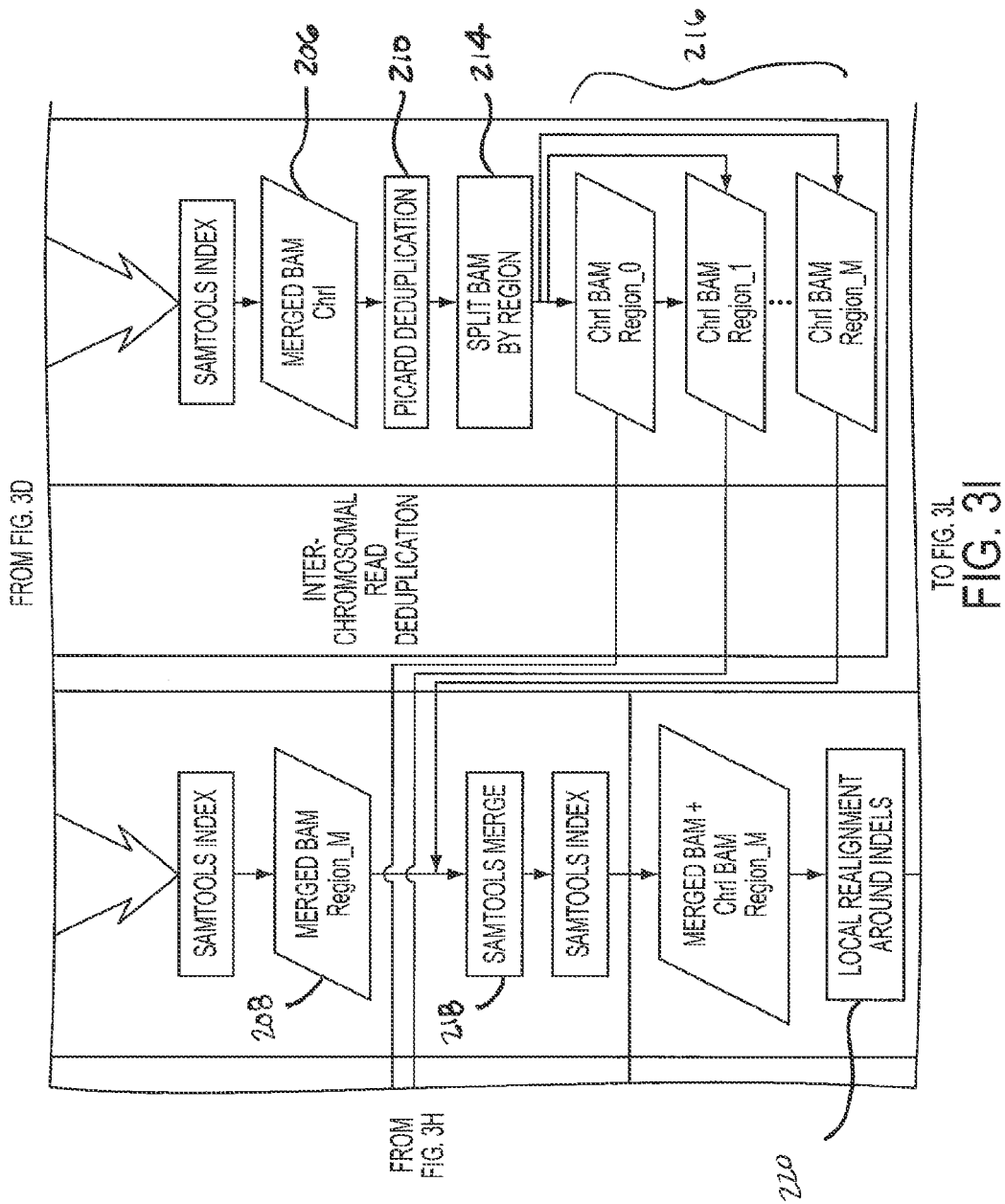

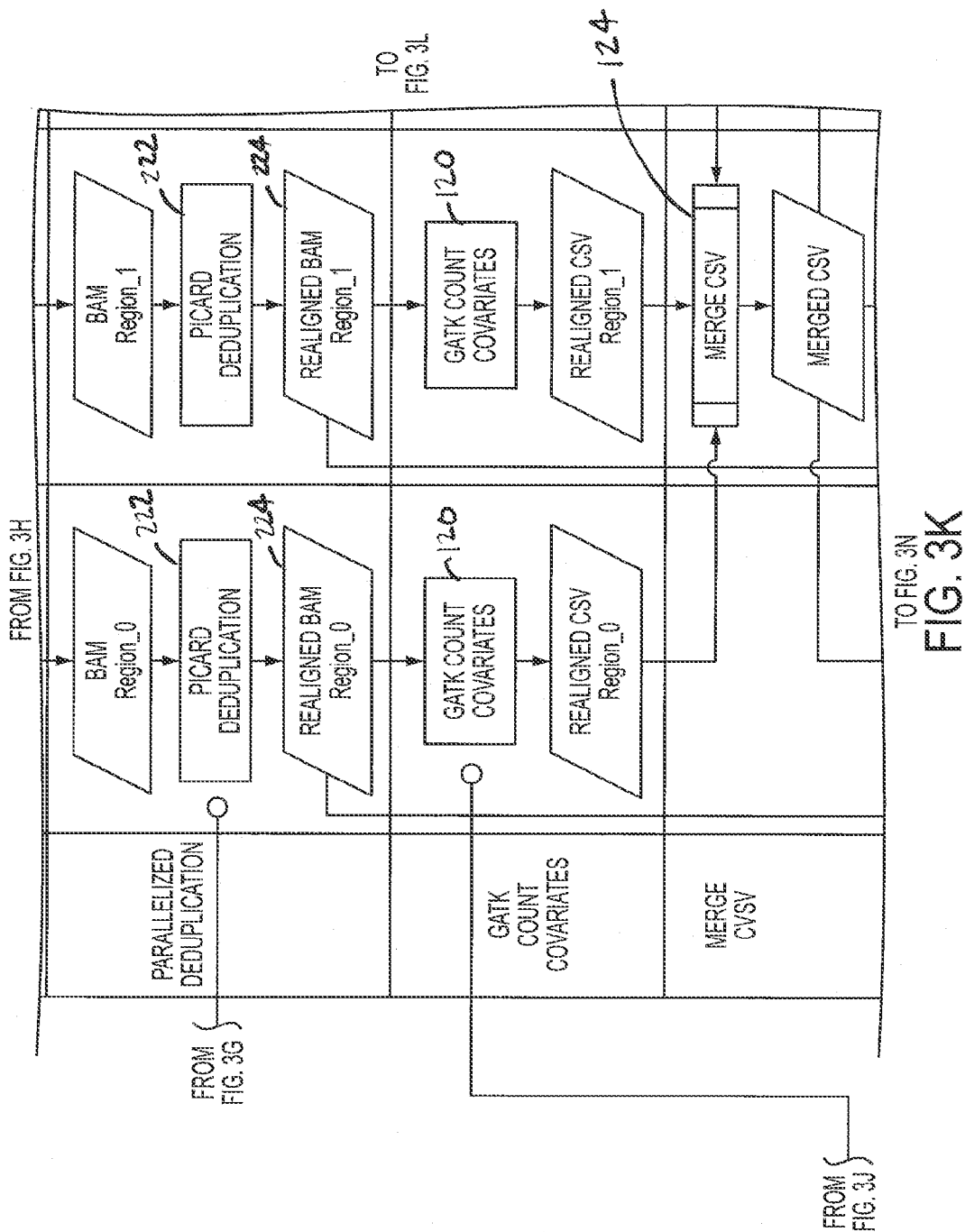

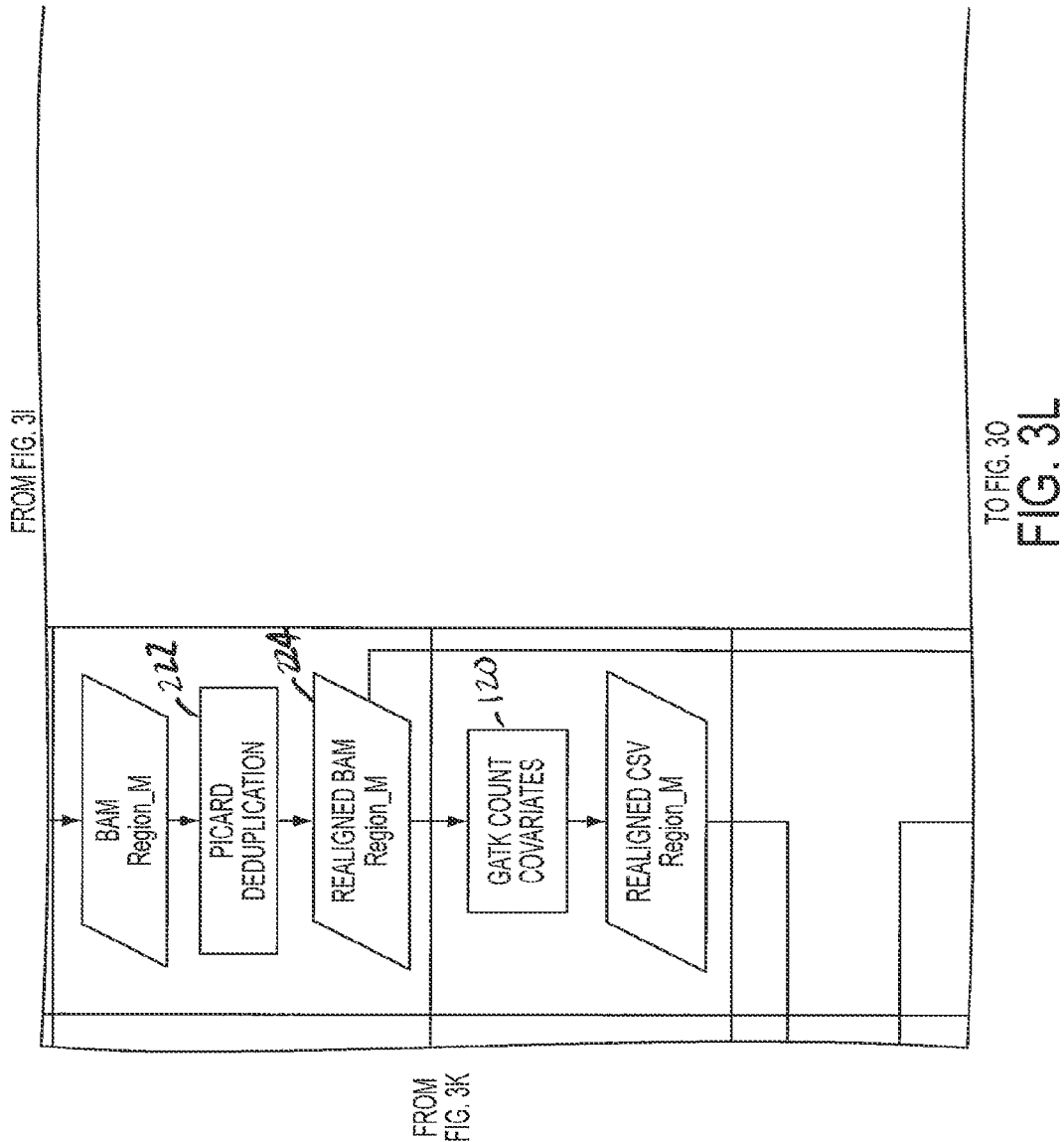

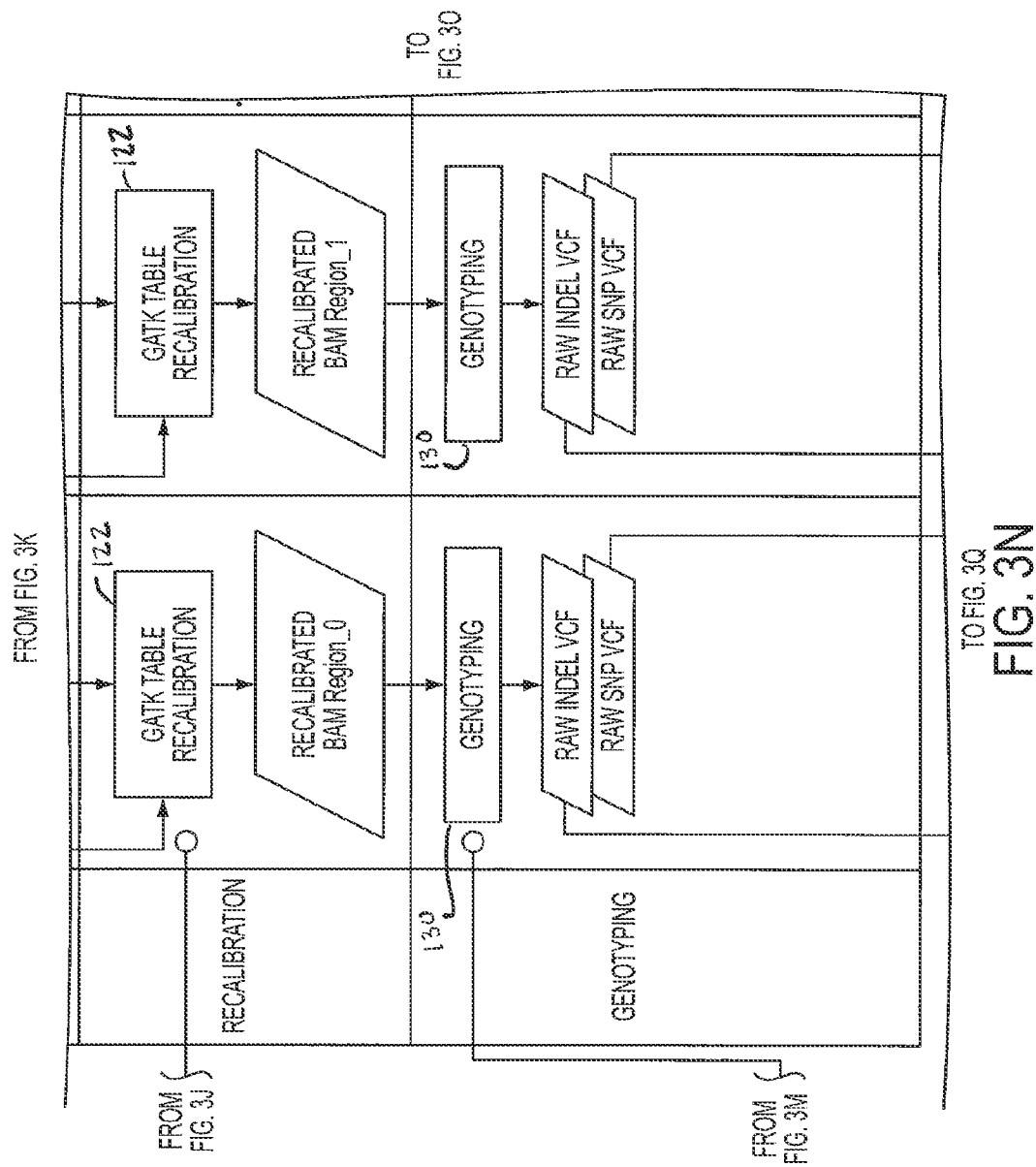

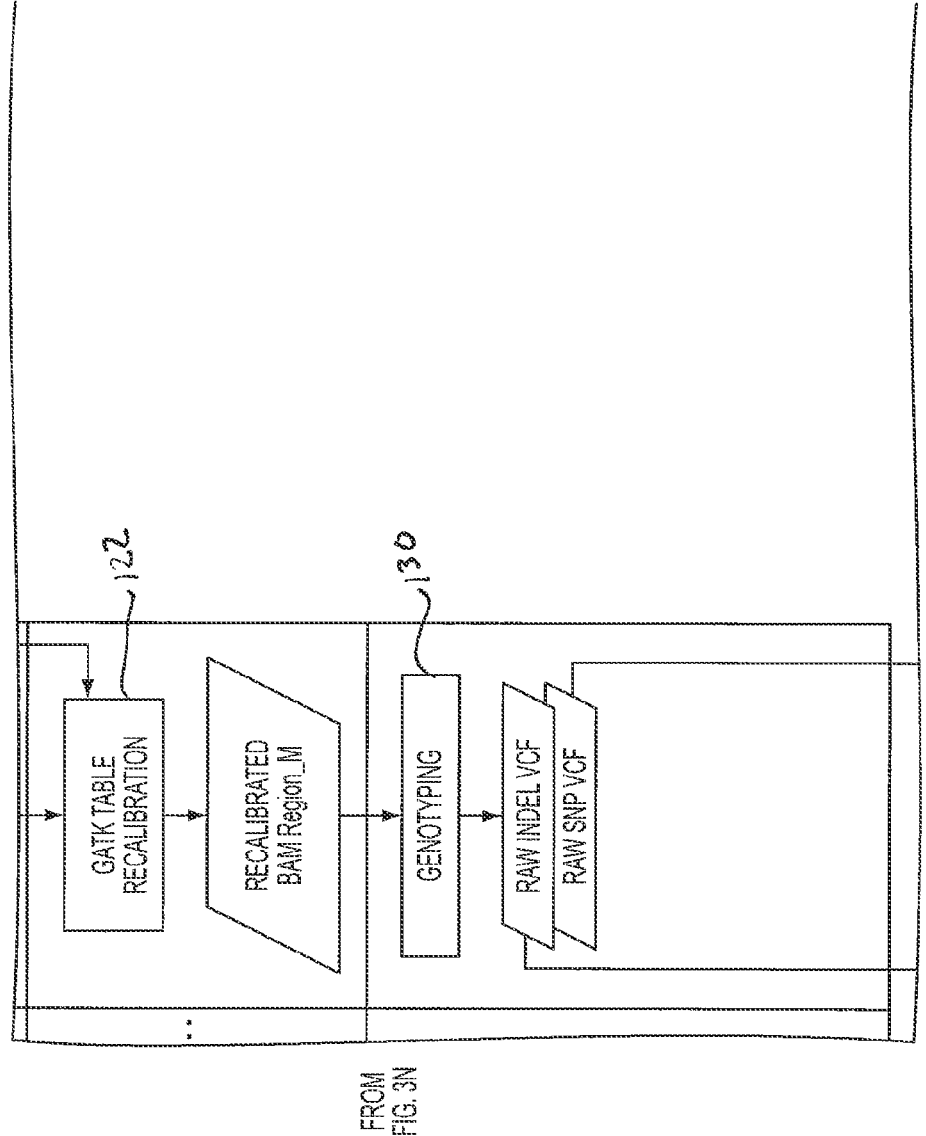

COMPREHENSIVE ANALYSIS PIPELINE FOR DISCOVERY OF HUMAN GENETIC VARIATION

CROSS-REFERENCE TO RELATED APPLICATIONS

The current application claims priority to U.S. Provisional Patent Application Ser. No. 61/611,960, filed Mar. 16, 2012, the disclosure of which is incorporated herein by reference.

FIELD OF THE INVENTION

The current disclosure represents an automated and comprehensive analysis tool for the discovery of human genetic variation, that is capable of running on all popular environments for parallelized computing, and utilizes a parallelization strategy that results in reduced analysis time, while improving data integrity and quality.

BACKGROUND OF THE INVENTION

Introduction to Discovery of Human Genetic Variation

Next generation sequencing (NGS) has revolutionized genetic research, empowering dramatic increases in the discovery of new functional variants in syndromic and common diseases. The technology has been widely adopted by the research community and is now seeing rapid adoption clinically, driven by recognition of NGS diagnostic utility and enhancements in quality and speed of data acquisition. Compounded by declining sequencing costs, this exponential growth in data generation has created a computational bottleneck. Current analysis approaches can take months to complete resulting in bioinformatics overheads that exceed raw sequencing costs and represent a significant limitation.

Biologists have set the expectation on the bioinformatician to transform these massive and complex raw human genomic data sets into accurately refined subsets from which they may derive meaningful insights. Sequencing the genomes from a single study can yield terabytes of read data which, in turn, is utilized to produce a list of variations comprising millions of single nucleotide polymorphisms (SNPs), insertions and deletions (INDELs). The quality and presentation of these datasets are paramount to the successful interpretation of the results by the researcher or clinician and will be an underlying theme in the success of personalized medicine.

Overview of an Exemplary NGS Data Analysis Workflow

Next generation sequencing (NGS) technologies have revolutionized genetic research and have empowered a dramatic increase in the discovery of new functional variants that are responsible for both Mendelian and common diseases. The output from NGS instrumentation is profoundly out-pacing Moore's Law, and currently a single Illumina Hiseq 2000 is capable of producing 600 billion bases of sequencing output in under two weeks. With the ever increasing rate at which NGS data is generated, it has become critically important to optimize the data processing and analysis workflow in order to bridge the gap between Terabytes of raw data and scientific knowledge discovery. In the case of deep whole human genome resequencing analysis, the analytical process to go from raw sequencing instrument output to variant discovery requires multiple computational steps (Fig. S1).

Primary analysis typically describes the process by which instrument-specific sequencing measures are converted into files containing the short read sequence data, including generation of sequencing run quality control metrics. For example, for the Illumina HiSeq 2000 platform, primary analysis encompasses the process of image analysis to generate intensities (BCL files), the conversion of these intensities into actual reads with base-quality scores (BCL conversion), and the generation of numerous metrics that allow for assessment of the quality of the run. These instrument specific primary analysis procedures have been well developed by the various NGS manufacturers and can occur in real-time as the raw data is generated. The community has adopted a human-readable primary analysis output format called Sanger FASTQ, containing read identifiers, the sequence of bases, and the PHRED-like quality score Q, represented by single character ASCII character to reduce the output file size {Cock, 2010 #425}.

Current best practice for deep whole human genome comparative sequencing (resequencing) requires that a sample be sequenced to a depth of at least 30× coverage. With the HiSeq instrument, primary analysis for resequencing produces ~1 billion short reads, giving a total of 100 giga base-pairs (Gb) of raw sequencer output. Secondary analysis encompasses both alignment of these sequence reads to the human reference genome and utilization of this alignment to detect differences between the patient sample and the reference. This process of detection of genetic differences, variant detection and genotyping, enables us to accurately use the sequence data to identify single nucleotide polymorphisms (SNPs), small insertions and deletion (indels) and structural changes in the DNA, such as copy number variants (CNVs) and chromosomal rearrangements. The most commonly utilized approach to secondary analysis incorporates five sequential steps: (1) initial read alignment; (2) local realignment around indels; (3) removal of duplicate reads; (4) recalibration of the base quality scores; and (5) variant discovery and genotyping (see, Depristo, M. A. et al. A framework for variation discovery and genotyping using next-generation DNA sequencing data. Nat Genet 43, 491-498 (2011), the disclosure of which is incorporated herein by reference). The final output of this process is a recalibrated analysis-ready variant call file (VCF), containing 3-4 million SNPs and INDELS, is then ready for the process of tertiary analysis, where an attempt is made to identify variants relevant to the patient's disease phenotype of interest.

Overview of Popular Software Tools

Popular utilization of next-generation sequencing for the identification of human genetic variation has led to the development of numerous tools to process raw sequencing data and subsequently identify polymorphisms. Analysis of sequencing data can be broken into two computational steps: alignment of the sequencing reads to a reference genome and variant calling from that alignment. A variety of aligners and variants callers exist, but few complete pipelines exist.

BWT-based (Bowtie, BWA) and hash-based (MAQ, Novoalign, Eland) aligners have been most successful so far. Among them BWA is a popular choice due to its accuracy, speed, the ability to take FASTQ (a text-based format for storing both a biological sequence and its corresponding quality scores) input and output data in Sequence Alignment/Map (SAM) format (a file generated by short read aligners containing alignments and other information—a BAM file is a compressed SAM file), and the open source nature.

Picard and SAMtools are typically utilized for the post-alignment processing steps and to output SAM binary (BAM) format files (See, Li, H. et al. The Sequence Alignment/Map format and SAMtools. Bioinformatics 25, 2078-2079 (2009), the disclosure of which is incorporated herein by reference).

Several statistical methods have been developed for genotype calling in NGS studies (see, Nielsen, R., Paul, J. S., Albrechtsen, A. & Song, Y. S. Genotype and SNP calling from next-generation sequencing data. Nat Rev Genet 12, 443-451 (2011).), yet for the most part, the community standard for human genome resequencing is BWA alignment with the Genome Analysis Toolkit (GATK) for variant calling (Depristo, 2011). Among the many publicly available variant callers, GATK has been used in the 1000 Genome Project. It uses sophisticated statistics in its data processing flow: local realignment, base quality score recalibration, genotying, and variant quality score recalibration. The results are variant lists with recalibrated quality scores, corresponding to different categories with different false discovery rates (FDR).

Annovar is a tool to add comprehensive annotation to variant list. It is written in Perl and regularly updated with new content.

The majority of studies utilizing next generation sequencing to identify variants in human diseases have utilized this combination of alignment with BWA, post alignment processing with SAMtools and variant calling with GATK (See, Gonzaga-Jauregui, C., Lupski, J. R. & Gibbs, R. A. Human genome sequencing in health and disease Annu Rev Med 63, 35-61 (2012), the disclosure of which is incorporated herein by reference). However, these tools were largely developed independently and lack integration, making it difficult for an experienced bioinformatician to implement them appropriately. Furthermore, for a typical human genome, the sequential data analysis process (FIG. S1) can take over a week to complete. These challenges have created the need for a pipeline that would both streamline the bioinformatics analysis required to utilize these tools and dramatically reduce the time taken to go from raw reads to variant calls.

SUMMARY OF THE INVENTION

Next generation sequencing (NGS) technologies have revolutionized genetic research and have empowered a dramatic increase in the discovery of new functional variants that are responsible for both Mendelian and common diseases. The output from NGS instrumentation is profoundly out-pacing Moore's Law, and currently a single Illumina Hiseq instrument is capable of producing 600 billion bases of sequencing output in under two weeks. Compounded by sharply falling sequencing costs, this exponential growth in NGS data generation has created a computational and bioinformatics bottleneck in which current approaches can take months to complete analysis and interpretation. This reality has created an environment where the cost of analysis exceeds the cost of physically sequencing the sample. To overcome these challenges the current disclosure describes a computational pipeline (which is often referred to, herein, as "Churchill") that may fully automate the multiple steps required to go from raw sequencing reads to comprehensively annotated genetic variants. Through implementation of novel parallelization approaches it has been found that testing of exemplary embodiments has shown a dramatic reduction in the analysis time from weeks to hours. Through comprehensive automation and parallelization of genome data analysis pipelines exemplary embodiments described herein present an elegant solution to the challenge of rapidly identifying human genetic variation in a clinical research setting. Exemplary embodiments described herein represent a fully automated and comprehensive analysis tool for the discovery of human genetic variation, that may be capable of running on all popular environments for parallelized computing, and utilize a novel parallelization strategy that results in drastically reduced analysis time.

An exemplary pipeline as described herein is capable of utilizing at least four parallelization environments: shared memory server with explicit task creation, shared memory server with task creation by GNU Make, HPC clusters that support distributed Make, such as PBS and SGE, and Hadoop cluster with MapReduce. It has been found that exemplary implementations have achieved more than a ten-fold speedup in the time required to complete the analysis compared to single-threaded workflow. Compared with GATK-Queue script, an exemplary workflow implementation described herein is simpler, faster, and more widely applicable to various shared memory/distributed High Performance Computing clusters. Furthermore, an exemplary modular pipeline described herein has been designed with the flexibility to incorporate other analysis tools as they become available.

As will be shown by the exemplary embodiments described herein, it is an aspect of the current disclosure for analyzing genetic sequence data including the steps of: (a) obtaining, by a computer system, genetic sequencing data pertaining to a subject; (b) splitting the genetic sequencing data into a plurality of segments; (c) processing the genetic sequencing data such that intra-segment reads, read pairs with both mates mapped to the same data set, are saved to a respective plurality of individual binary alignment map (BAM) files corresponding to that respective segment; (d) processing the genetic sequencing data such that inter-segment reads, read pairs with both mates mapped to different segments, are saved into at least a second BAM file; and (e) processing at least the first plurality of BAM files along parallel processing paths. In a more detailed embodiment, the plurality of segments corresponds to a corresponding plurality of chromosomes. In a further detailed embodiment, the plurality of segments corresponds to segments of one more chromosomes or any given number of genomic subregions.

In an alternate detailed embodiment, the method further includes the steps of performing a de-duplication process on the second BAM file to produce deduplicated inter-segment reads; and merging the deduplicated inter-segment reads back into the respective plurality of BAM files corresponding to segments from with the inter-segment reads have been obtained. In a further detailed embodiment, the processing step (e) includes a step of local realignment on each of the first plurality of BAM files. Alternatively, or in addition, the processing step (e) includes a step of duplicate read removal on each of the first plurality of BAM files. Alternatively, or in addition, the processing step (e) includes a step of base quality score recalibration on each of the first plurality of BAM files. Alternatively, or in addition, the processing step (e) includes a step of variant calling on each of the first plurality of BAM files.

In an alternate detailed embodiment, the number of segments in the splitting step (b) is defined by the size of the genome and the number of respective processor cores available. Alternatively, or in addition, the segments in the splitting step (b) are of the same size. Alternatively, or in addition, the plurality of the segments in the splitting step (b) includes two or more genomic sub-regions. Alternatively, or in addition, each parallel processing path in step (e) corresponds to a respective processor core, and the number of segments in the splitting step (b) corresponds to a number of processor cores performing the processing step (e).

It is a further aspect of the current disclosure to provide a method for improving the processing efficiency of analyzing genetic sequence data of a human that includes: obtaining, by a computer system, genetic sequencing data from a subject (which may include raw sequencing reads at some point in the process) and analyzing the obtained genetic sequence data by the computer system, where the analyzing step involves dividing at least certain processing steps in the analysis among a plurality of parallel processing paths. In a more detailed embodiment the parallel processing paths may correspond, at least in part to at least some of 22 autosomal chromosomes, 2 sex chromosomes, and/or 1 mitochondria DNA. In a further detailed embodiment, the analyzing step may include at least 25 parallel processing paths, where each of the at least 25 parallel processing paths corresponding to a respective one of the plurality of 22 autosomal chromosomes, 2 sex chromosomes, and 1 mitochondria DNA. Alternatively, or in addition, the parallel processing paths may further correspond to read pairs with both mates mapped to different chromosomes.

It is a further aspect of the current disclosure to provide a method for improving the processing efficiency of analyzing genetic sequence data of any species for which a known genetic reference exists. The method described herein is applicable to not only the human genome, but could be used for variant discovery in any species, including but not limited to bacteria, plants and mammals.

In another alternative embodiment of the this aspect, the analyzing step may include at least one sub-step divided into at least 25 parallel processing paths, where each of the at least 25 parallel processing paths respectively correspond to 22 autosomal chromosomes, 2 sex chromosomes, and 1 mitochondria DNA. In a more detailed embodiment, the at least one sub-step may include a step of local realignment. Alternatively, or in addition, the at least one sub-step may include a step of unified genotyper. Alternatively, or in addition, the at least one sub-step may include a step of marking duplicates. Alternatively, or in addition, the analyzing step may include at least 26 parallel processing paths respectively corresponding to 22 autosomal chromosomes, 2 sex chromosomes, 1 mitochondria DNA, and 1 corresponding to read pairs in which both mates are mapped to the different chromosomes.

In another alternative embodiment of this aspect, the analyzing step may involve a step of mapping reads to a reference genome, where the step of mapping reads to the reference genome may also be divided into a plurality of parallel processing paths.

In another alternative embodiment of this aspect, the method may include processing a plurality of subsets of the genetic sequence data among the plurality of parallel processing paths. In a more detailed embodiment, the plurality of subsets of the genetic data may be in the form of binary alignment map (BAM) files at least at some point in the respective parallel processing paths. In a further detailed embodiment, the BAM files may include a first plurality of BAM files corresponding to read pairs in which both mates are mapped to the same data set, and at least one BAM file corresponding to read pairs in which both mates are mapped to different data sets. In a further detailed embodiment, the first plurality of BAM files may corresponding to one or more segments of chromosomes with both mates mapped to the respective segments of chromosomes in each BAM file. In a further detailed embodiment, the total number of parallel processing paths may correspond to the number of processor cores respectively performing the parallel processing operations.

In an alternate detailed embodiment, the BAM files may include at least twenty-six BAM files, 22 corresponding to autosomal chromosomes, 2 corresponding to sex chromosomes, 1 corresponding to mitochondria DNA, and 1 corresponding to read pairs in which both mates are mapped to the different chromosomes. Alternatively or in addition, the processing of a plurality of subsets of the genetic sequence data among the plurality of parallel processing paths may include a step of spawning multiple processes using the xargs utility in the Linux environment; and/or may include a step of utilizing GNU parallel processing; and/or may include a step of performing the parallel processing in a distributed cluster environment; and/or may include a step of utilizing distributed Make utilities; and/or may include a step of performing parallel processing in utilizing a distributed file system. Alternatively, or in addition, the processing a plurality of subsets of the genetic sequence data among the plurality of parallel processing paths may be performed utilizing a cloud computing environment, If in a distributed cluster environment, the processing may include submitting jobs to a job queue and managing the executions of the jobs by a job scheduler. In a more detailed embodiment, the jobs may be submitted in a manner so as to maintain task dependency. In an even more detailed embodiment, the jobs may be synchronized to maintain task dependency or the jobs may be submitted with dependency directions so as to maintain task dependency.

If the process utilizes distributed Make utilities, then such utilities may include qmake in the SGE environment or distmake in the SGE or PBS environment.

If the process utilizes a distributed file system, then the distributed file system may involve a MapReduce framework.

As will be shown by the exemplary embodiments described herein, it is another aspect to provide a method for analyzing genetic sequence data that includes the steps of: obtaining, by a computer system, genetic sequencing data from a subject; processing the genetic sequencing data such that read pairs with both mates mapped to the same segment of genetic sequence data are saved to an individual chromosomal (or intra-segmental) binary alignment map (BAM) file corresponding to that segment; processing the genetic sequencing data such that read pairs with both mates mapped to different segments of genetic sequence data are saved into an inter-chromosomal (or inter-segmental) BAM file; and processing the chromosomal (or intra-segmental) and inter-chromosomal (or inter-segmental) BAM files along parallel processing paths. In a more detailed embodiment, the processing of chromosomal (or intra-segmental) and inter-chromosomal (or inter-segmental) BAM files along parallel processing paths includes a step of duplicates removal, producing a corresponding plurality of de-duplicated chromosomal and inter-chromosomal BAM files. In a further detailed embodiment, the method further includes the step of merging reads from the inter-chromosomal (or inter-segmental) de-duplicated BAM file into the de-duplicated chromosomal BAM files.

Alternatively, or in addition, with the method of this aspect, the subject may be a human subject.

BRIEF DESCRIPTION OF THE DRAWINGS

FIG. 2A is the portion of the parallelized work-flow diagram to the left of the portion set forth in FIG. 2B; and FIG. 2B is a portion of the portion of the parallelized work-flow diagram to the right of the portion set forth in FIG. 2A;

FIG. 3A is a portion of the parallelized work-flow diagram to the left of the portion set forth in FIG. 3B; FIG. 3D is a portion of the parallelized work-flow diagram to the right of the portion set forth in FIG. 3C and above the portion set forth in FIG. 3I; FIG. 3I is a portion of the parallelized work-flow diagram below the portion set forth in FIG. 3D, to the right of the portion set forth in FIG. 3H and above the portion set forth in FIG. 3L; FIG. 3K is a portion of the parallelized work-flow diagram to the right of the portion set forth in FIG. 3G, above and to the right of the portion set forth in FIG. 3J, to the left of the portion set forth in FIG. 3L, below the portion set forth in FIG. 3H and above the portion set forth in FIG. 3N; FIG. 3L is a portion of the parallelized work-flow diagram to the right of the portion set forth in FIG. 3K, below the portion set forth in FIG. 3I and above the portion set forth in FIG. 3O; FIG. 3N is a portion of the parallelized work-flow diagram to the right of the portion set forth in FIG. 3J, above and to the right of the portion set forth in FIG. 3M, below the portion set forth in FIG. 3K, above the portion set forth in FIG. 3Q and to the left of the portion set forth in FIG. 3O; FIG. 3O is a portion of the parallelized work-flow diagram to the right of the portion set forth in FIG. 3N, below the portion set forth in FIG. 3L and above the portion set forth in FIG. 3R; FIG. 3R is a portion of the parallelized work-flow diagram to the right of the portion set forth in FIG. 3Q and below the portion set forth in FIG. 3O;

FIG. 5A provides a diagram illustrating the parallel processing region sizes for embodiments which break according to chromosomes and FIG. 5B provides a diagram illustrating the parallel processing region sizes for embodiments which break according to smaller regions;

DETAILED DESCRIPTION

Figure 1:
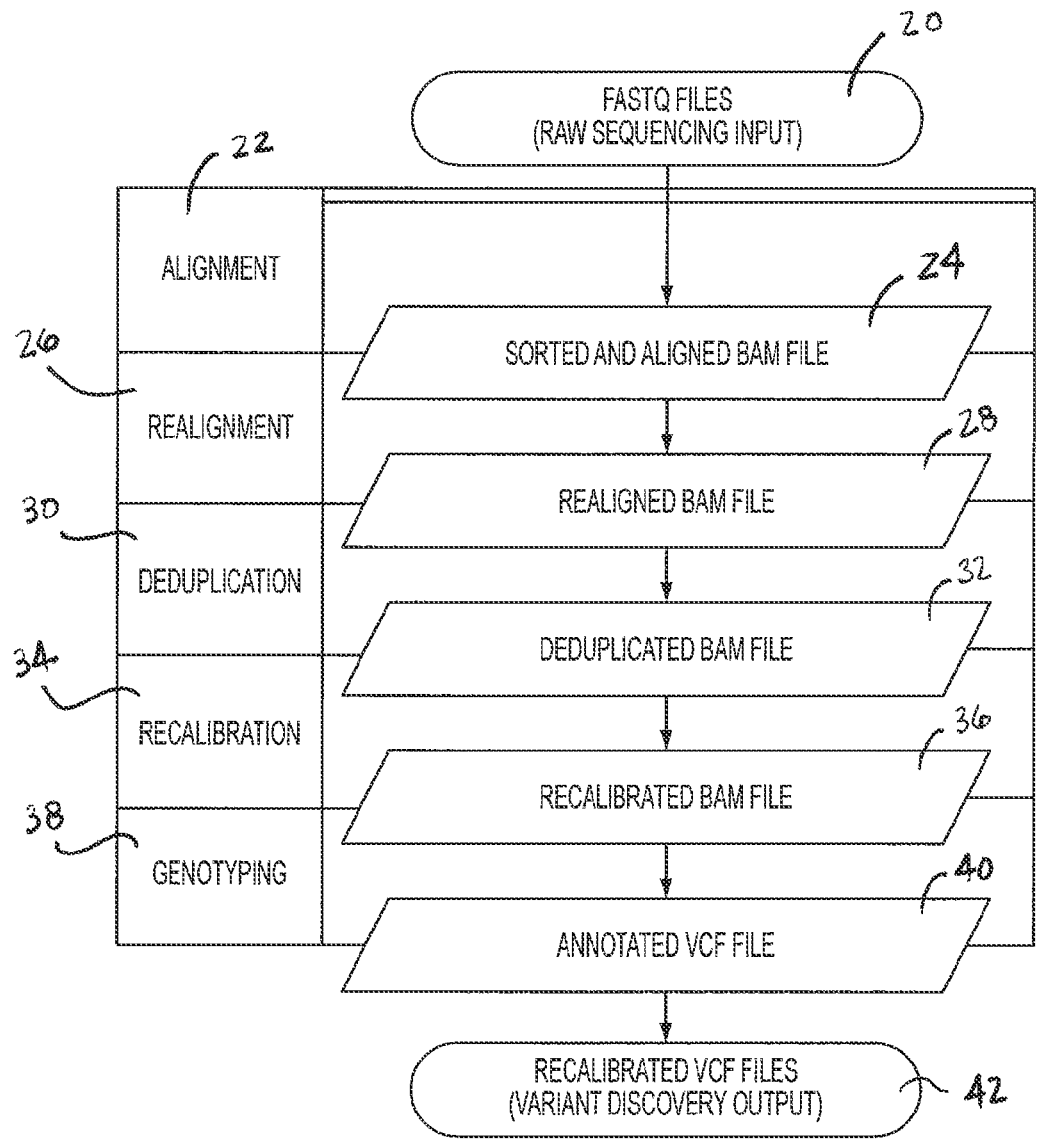
FIG. 1 provides a block-diagram, flow representation of a prior art single-threaded work flow.

Single-Threaded Workflow—FIG. 1

A single-threaded workflow is illustrated in FIG. 1. Analysis may begin with the raw sequencing reads in the FASTQ format as shown in block 20. Data may be generated from the Illumina HiSeq 2000 by the Biomedical Genomics Core, and FASTQ files may be produced by CASAVA 1.8.2's BCL Conversion. By default CASAVA saves 4 million reads in one file, so all files may be concatenated for each read direction into a single FASTQ file.

BWA may be used for initial mapping of the reads to the reference genome. An aggressive threshold may be chosen for base quality trimming, i.e., q=15. This option may result more correctly aligned bases because more results are mapped due to the trimming of low quality ends. After running BWA aln on each read direction BWA sample may be used to produce alignment output in SAM format, which may then be converted to BAM and sorted by coordinate using SAMTools. The alignment step is shown in block 22 to produce sorted and aligned BAM files 24.

Next the MarkDuplicates tool of Picard may be used to remove possible PCR and optical duplicates. The deduplication step is shown in block 30.

For variant calling and genotyping, GATK (version 1.6) may be used. First, local realignment (block 26) may be performed to improve the alignment of reads that were initially mapped around indels, producing realigned BAM files 28. Next Picard Tools MarkDuplicates (version 1.67) <http://picard.sourceforge.net> may be used to remove possible PCR and optical duplicates. Base quality score recalibration 34 may be applied to adjust the base quality scores originally set by the base calling software of the HiSeq instrument, producing recalibrated BAM files 36. Unified Genotyper 38 may subsequently called to produce raw SNP and indel calls. Finally, variant quality score recalibration may be performed on the raw variant calls. The final output of the GATK analysis is a variant call format (VCF) file 42, containing a comprehensive list of variants divided into different categories corresponding to different sensitivity and specificity levels.

Annovar may be used to annotate this variant list; gene-based, region-based, and filter-based annotations may be performed. Finally, the annotated variant list may be converted into a spreadsheet that is analysis ready, in a format that can be readily accessible and manipulated by the researchers or clinicians.

Identifying Dependency Among Steps

Each of the required data processing steps were carefully examined and optimal approaches for parallelized processing were determined. Alignment of individual reads to a reference genome is considered to be an embarrassingly parallel process as the 1 billion raw reads that are generated in sequencing a human genome can in theory be mapped to the reference genome independently of one another; the only constraint for paired-end reads is that both reads in a pair should be correctly oriented within proper distance. The remaining steps in the analysis workflow are not embarrassingly parallel by nature and, as such, required the development of novel approaches to achieve parallelization. One approach to enable a modest level of parallelization of the subsequent steps is to divide the analysis by individual chromosomes (22 autosomes (chromosomes 1 to 22) and two sex chromosomes (chromosomes X and Y)). However, doing so results in a significant load imbalance as the size of these chromosomes varies significantly, with chromosome 1 being ~5 times larger than chromosome 21 (See FIGS. 5A and 5B). In addition, limiting parallelization at chromosomal level restricts the use of processors to a total of 24, such that utilization of more than 24 processors cannot improve performance.

Dependencies among these steps may be identified as a starting point for the workflow optimization. The nature of NGS data generation implies that the reads can be mapped to the reference genome independently of one another; the only constraint for paired-end reads is that both reads in a pair should be properly oriented within proper distance. Table 1 summarizes these various steps and the prerequisites.

TABLE 1

Various steps of the analysis pipeline and their prerequisites.

| Step | Prerequisites |
| --- | --- |
| FASTQ Filtering | None |
| BWA | FASTQ Filtering. Additionally, each read in a pair must be mapped before BWA sampe and BAM conversion and sorting |
| Local Realignment | Sorted BAM |
| Duplicates removal | Local Realigned BAM |
| Base Quality Score Recalibration | Duplicates-removed BAM |
| Genotypinh | Recalibrated BAM |
| Variant Quality Score Recalibration | Raw variant list |
| Annotation | Recalibrated variant list |

Identifying Steps that can Run Simultaneously

FIG. 2: Parallelization Diagram

Figure 2A:
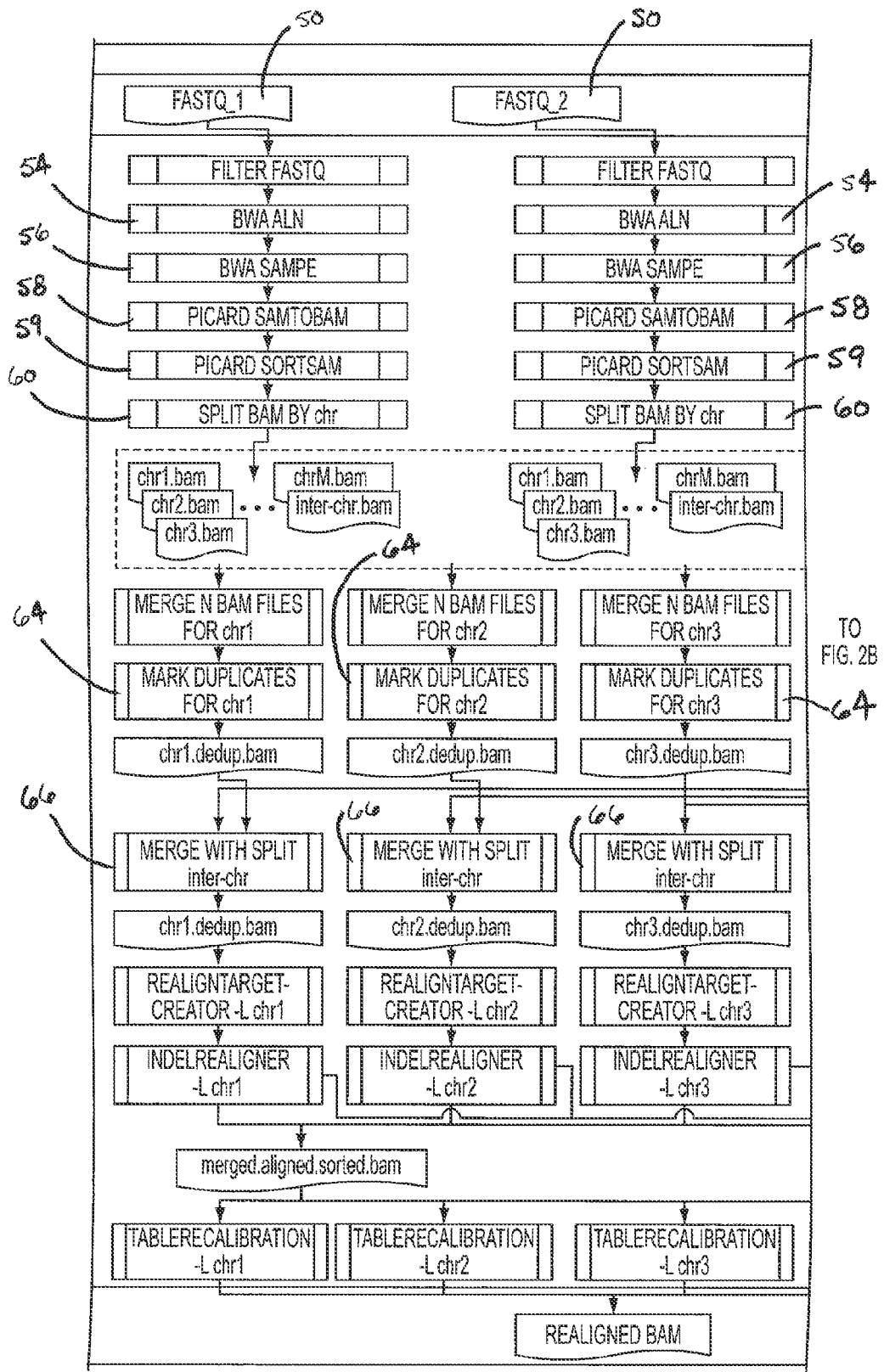
FIGS. 2A-2B provide a block-diagram, flow representation of a parallelized work flow according to an embodiment of the current disclosure.
Figure 2B:
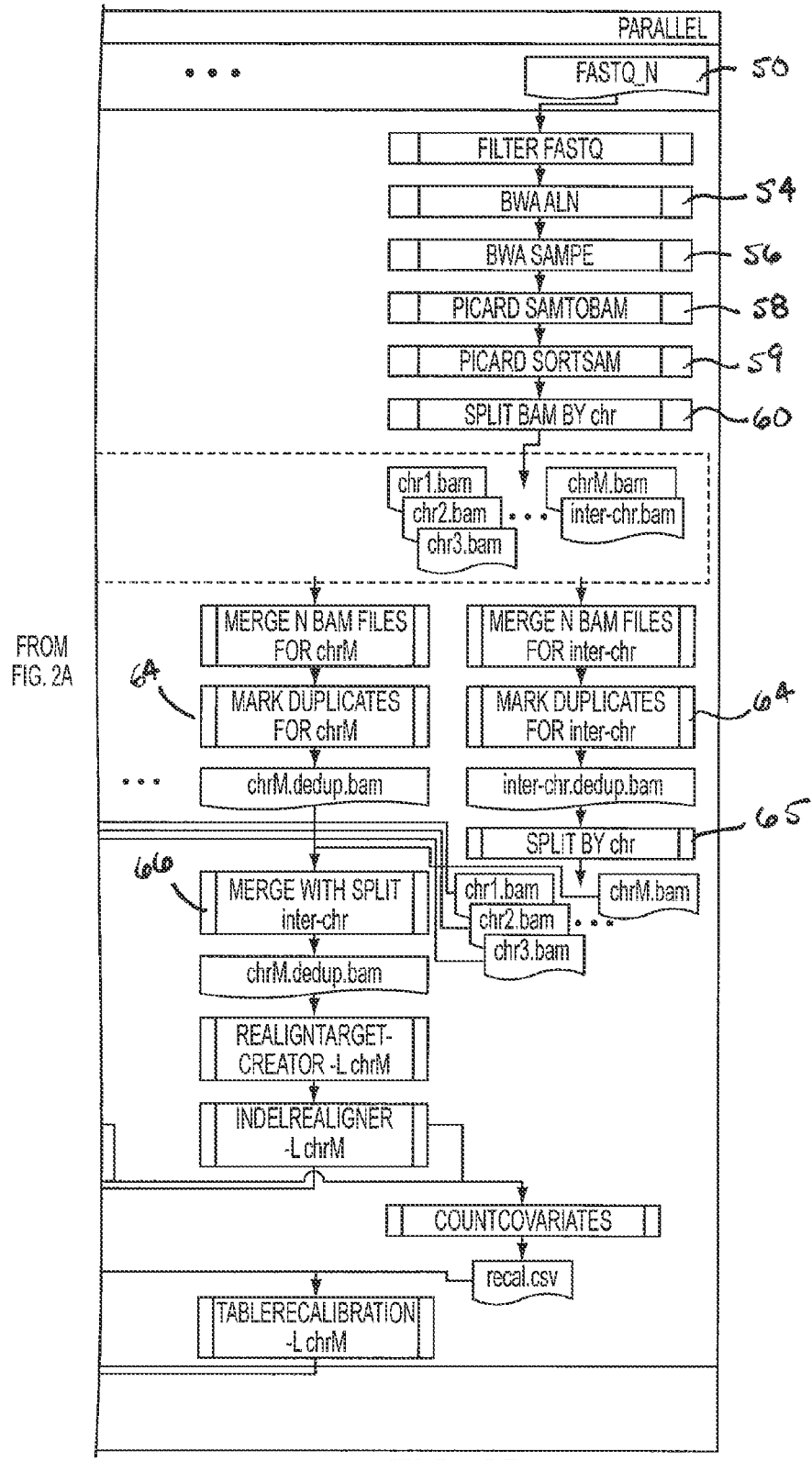

Based on the dependency table above, the flowchart of FIG. 2 (FIGS. 2A and 2B) was created to highlight steps that can run in parallel.

BWA can run in N jobs, where N is the number of paired-end FASTQ files 50. In CASAVA 1.8.2 this is controlled by BCL Conversion's parameter—fastq-cluster-count, which specifies the maximum number of clusters per output FASTQ file. It was found the default value of 4,000,000 worked reasonably well for current settings.

All other steps, however, are not as embarrassingly parallel and cannot be split in a similar way. Fortunately, the human genome contains 24 chromosomes, which facilitates a natural way to run the tasks independently on individual chromosomes. The steps that can be parallelized by chromosome include local realignment and unified genotyper.

Duplicates removal, base quality score recalibration, and variant quality score recalibration fall in a third category that cannot be naively parallelized. For paired-end reads with both mates mapped to the same chromosome, it is possible to mark duplicates on individual chromosomes; however, reads with mates mapped to different chromosome provide important information about possible inter-chromosomal rearrangement and should not be simply discarded. In order to keep these reads while enabling per-chromosome duplicates removal, a method for combining the steps was developed as follows:

Initially, steps such as running BWA aln, running BWA sampe 56, running Picard SAM to BAM 58, and running Picard sort SAM 59 may be processed in parallel according to respective FASTQ files 50.

Split by Chromosome.

Read pairs with both mates mapped to the same chromosome are saved to an individual BAM file as shown by step 60. For human genome this results in 25 files (chr1.bam, chr2.bam, . . . , chr22.bam, chrX.bam, chrY.bam, and chrM.bam, including 22 autosomal chromosomes, 2 sex chromosomes, and mitochondria DNA). In addition, read pairs with both mates mapped to different chromosomes are saved in a separate BAM file, identified in FIG. 2 by inter-chr.bam (or chrI.bam in other embodiments—"I" is short for inter-chromosomal mapping).

Duplicates Removal for Each Chromosome.

Each of the 26 BAM files from the previous split step undergoes Picard Tools' MarkDuplicates processing independently in step 64, to produce chr1-dedup.bam, chr2-dedup.bam, . . . , chr22-dedup.bam, chrX-dedup.bam, chrY-dedup.bam, chrM-dedup.bam, and inter-chr.dedup.bam (or chrI-dedup.bam).

Merge by Chromosome.

De-duplicated inter-chromosomal reads are merged back the de-duplicated reads for each chromosome in step 66 (after splitting the inter-chr.bam file according to each chromosome in step 65). The results are 25 BAM files, one for every chromosome (chr1.dedup.bam, .chr2.dedup.bam, chr3.dedup.bam and chrM.dedup.bam). These 25 BAM files may be processed along parallel pathways to perform the realignment steps, base quality score recalibration steps, genotyping steps and variant quality score recalibration steps.

Parallel Processing—Different Ways to Create New Tasks.

Figure 3A:
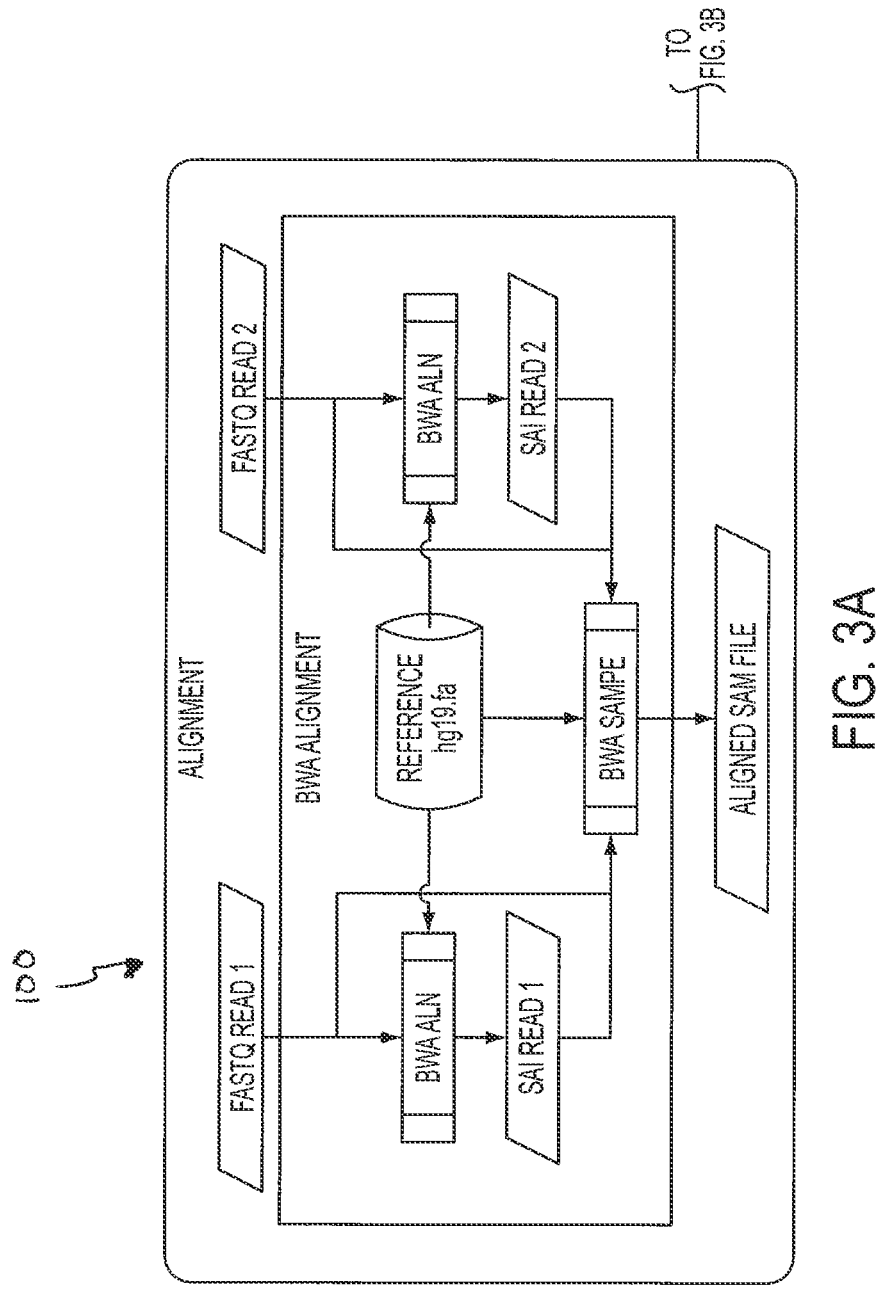
FIGS. 3A-3R provide a block-diagram, flow representation of a parallelized work flow according to another embodiment of the current disclosure.
Figure 3B:
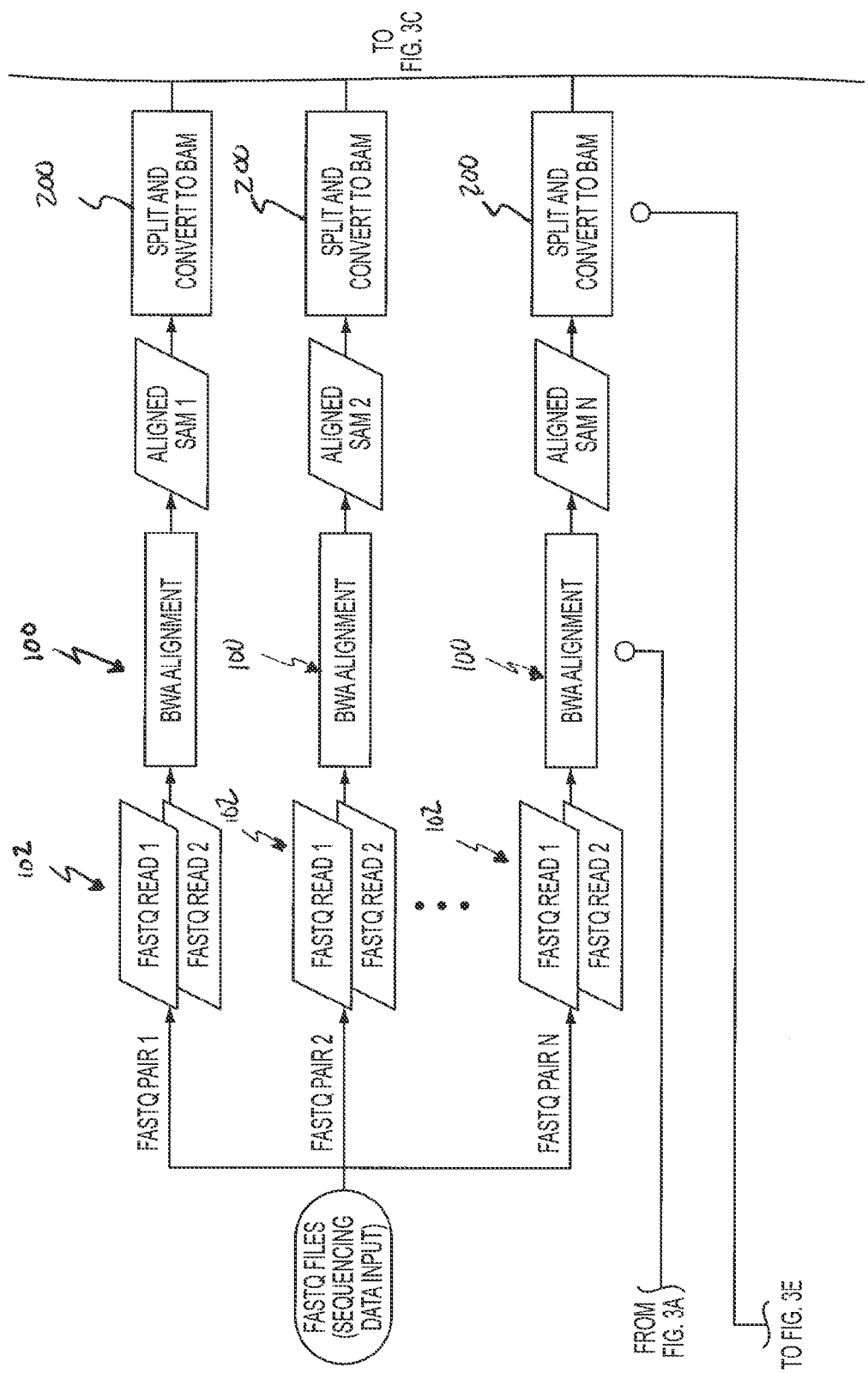
FIG. 3B is a portion of the parallelized work-flow diagram to the left of the portion set forth in FIG. 3C, to the right of the portion set forth in FIG. 3A and above the portion set forth in FIG. 3E.
Figure 3C:
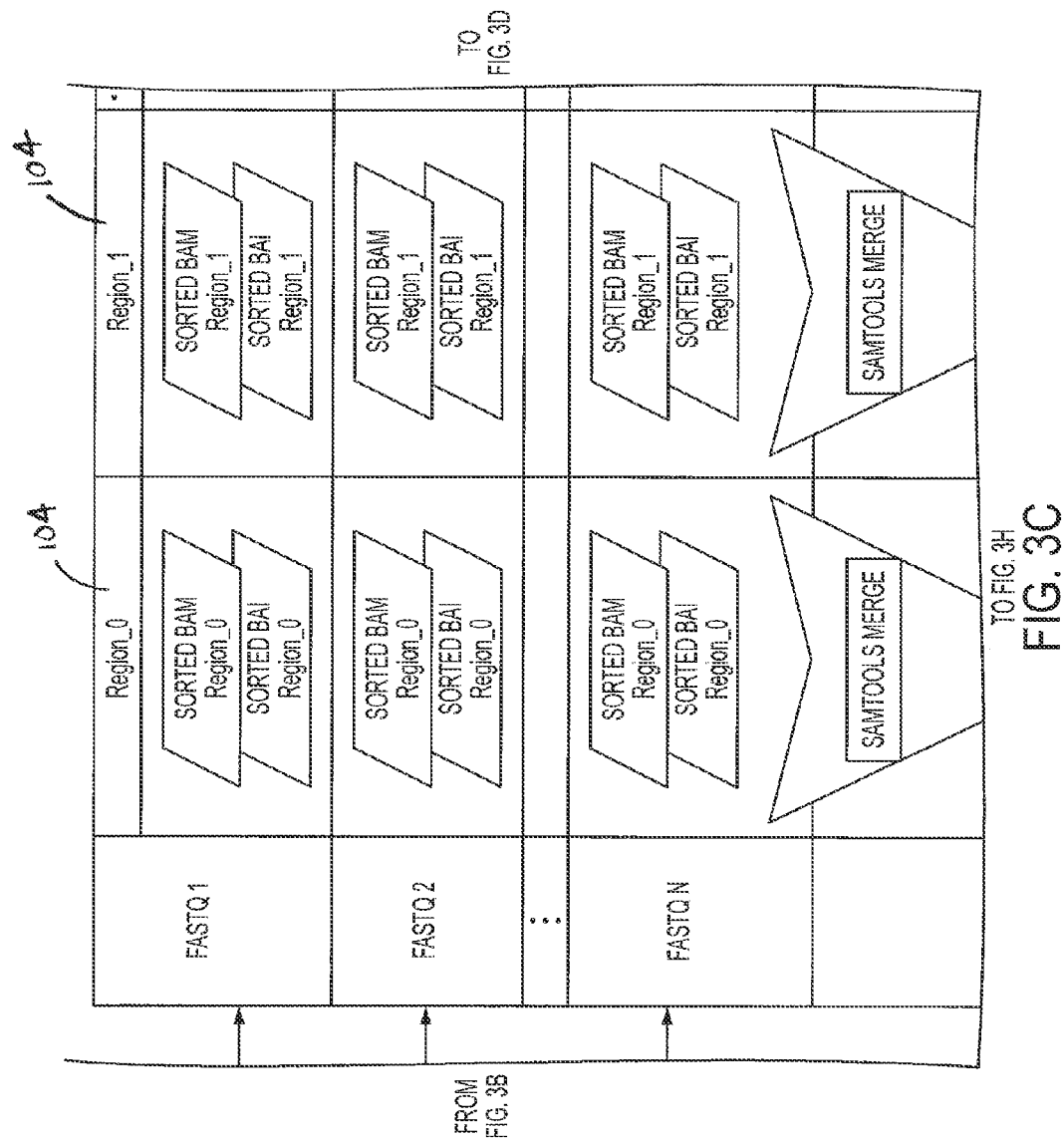
FIG. 3C is a portion of the parallelized work-flow diagram to the right of the portion set forth in FIG. 3B, to the left of the portion set forth in Fig. D and above the portion set forth in FIG. 3H.
Figure 3E:
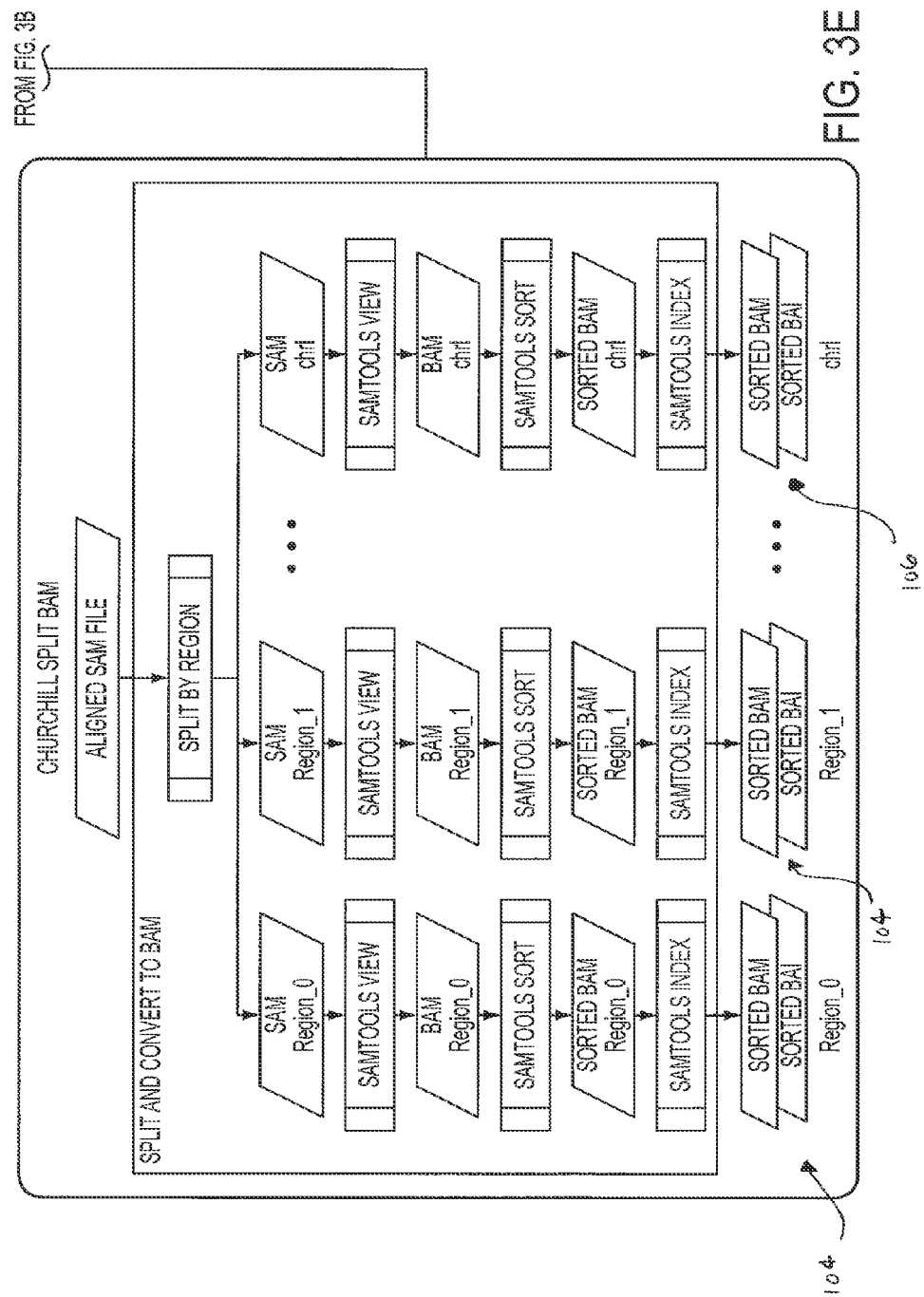
FIG. 3E is a portion of the parallelized work-flow diagram below and to the left of the portion as set forth in FIG. 3B.
Figure 3F:
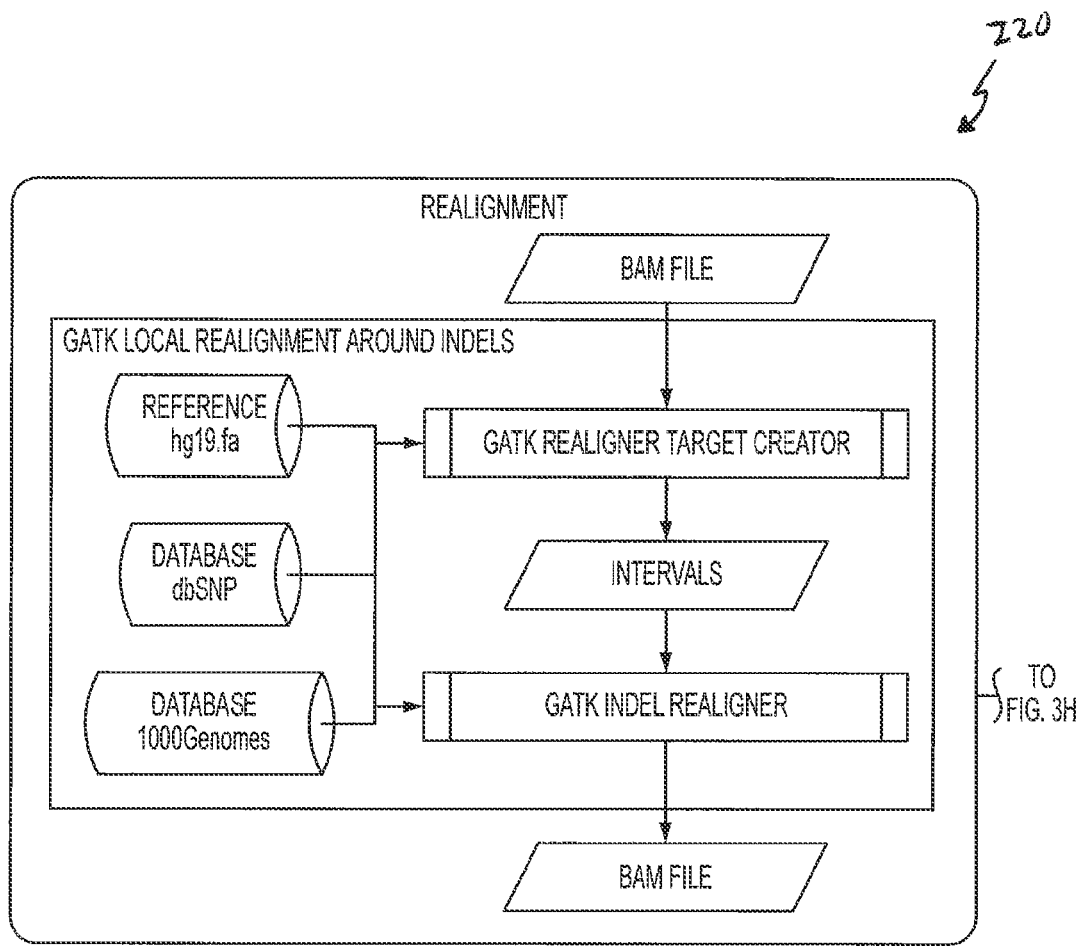
FIG. 3F is a portion of the parallelized work-flow diagram to the left of the portion set forth in FIG. 3H.
Figure 3G:
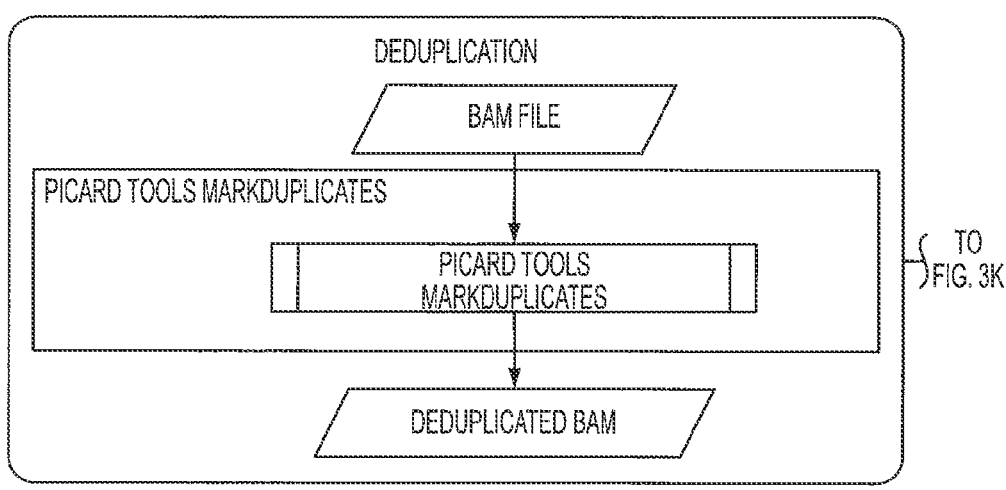
FIG. 3G is a portion of the parallelized work-flow diagram to the left of the portion set forth in FIG. 3K.
Figure 3H:
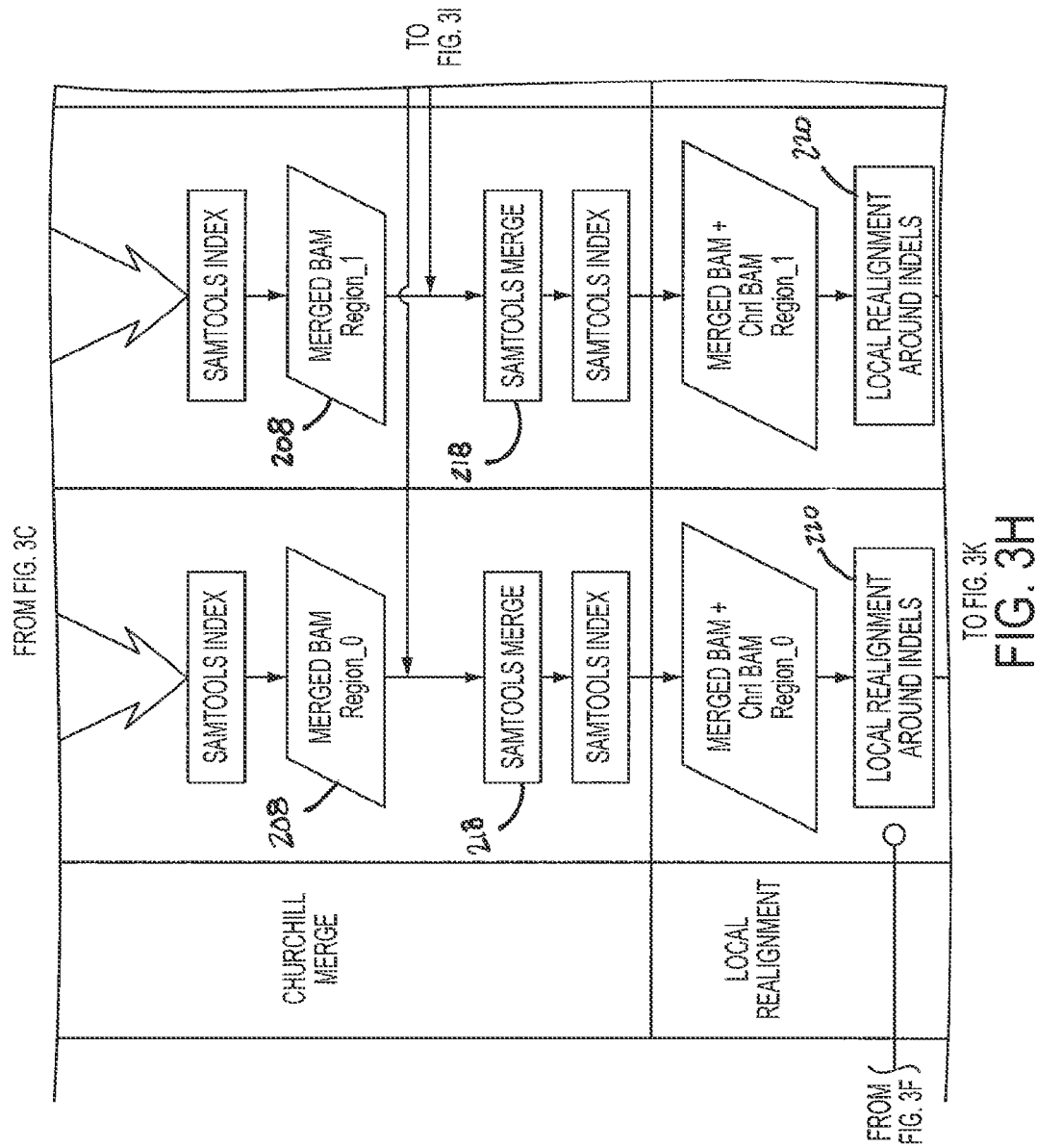
FIG. 3H is a portion of the parallelized work-flow diagram to the right of the portion set forth in FIG. 3F, to the left of the portion set forth in FIG. 3I, below the portion set forth in FIG. 3C and above the portion set forth in FIG. 3K.
Figure 3J:
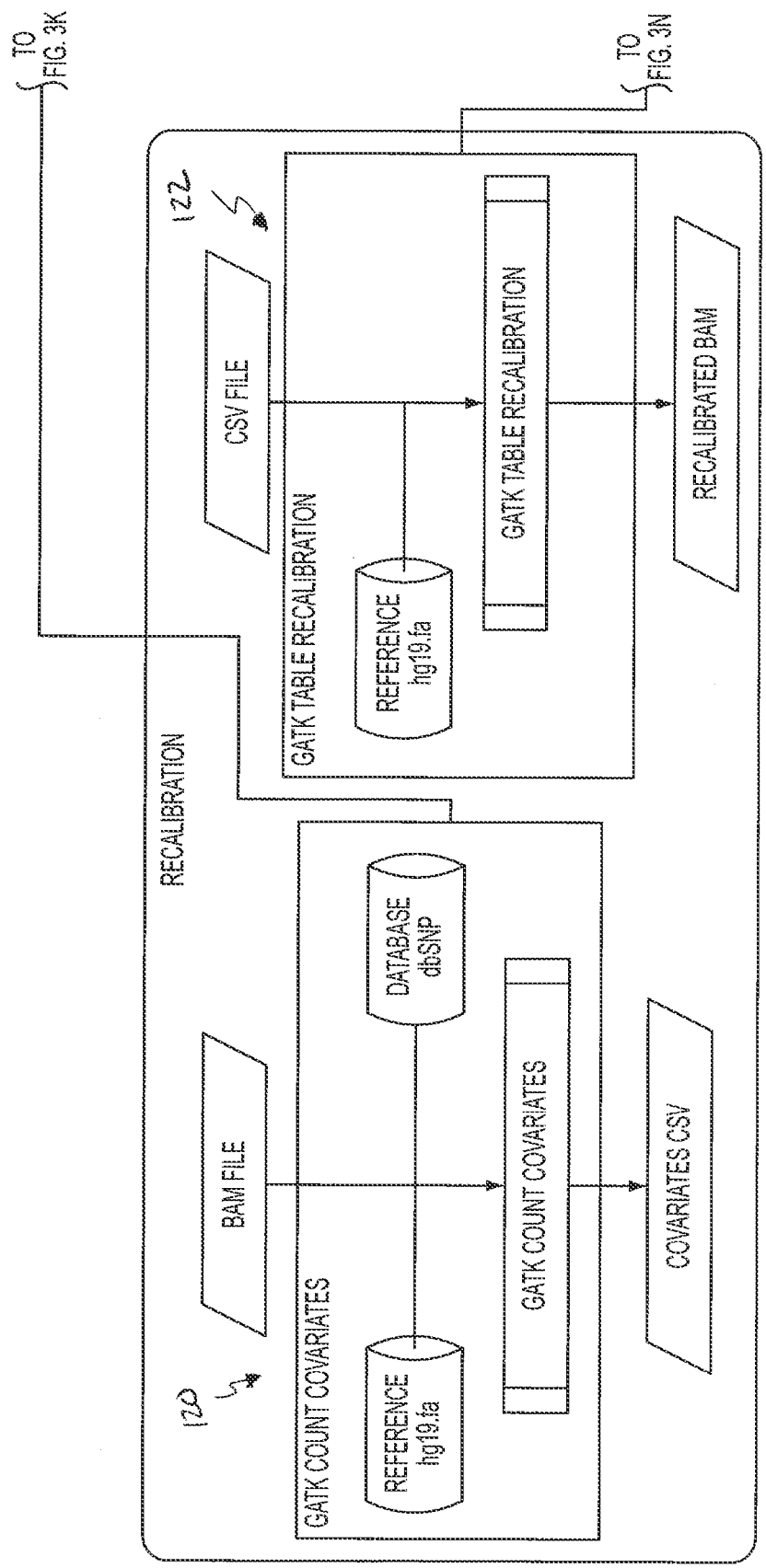
FIG. 3J is a portion of the parallelized work-flow diagram below and to the left of the portion set forth in FIG. 3K and to the left of the portion set forth in FIG. 3N.
Figure 3M:
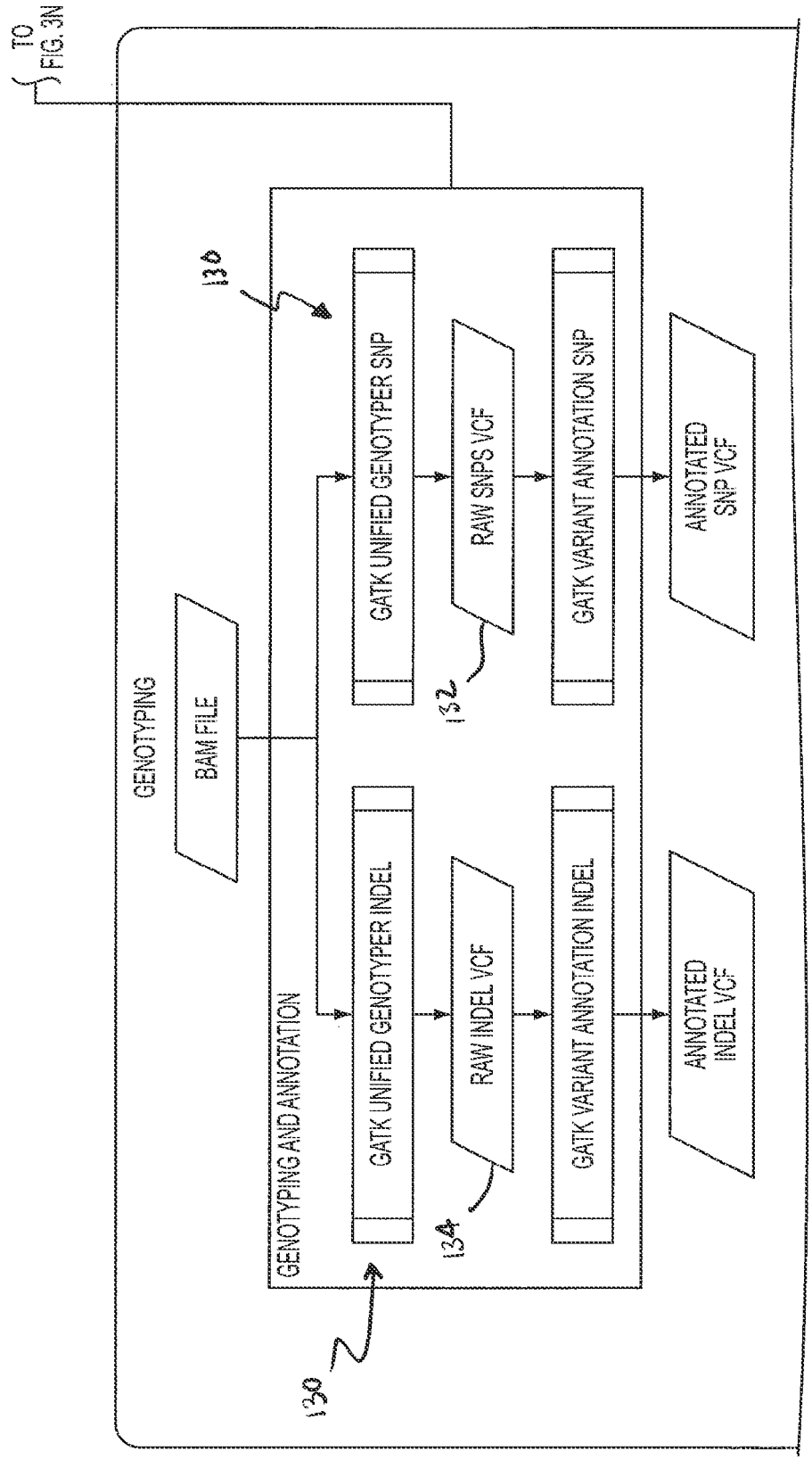
FIG. 3M is a portion of the parallelized work-flow diagram below and to the left of the portion set forth in FIG. 3N and above the portion set forth in FIG. 3P.
Figure 3P:
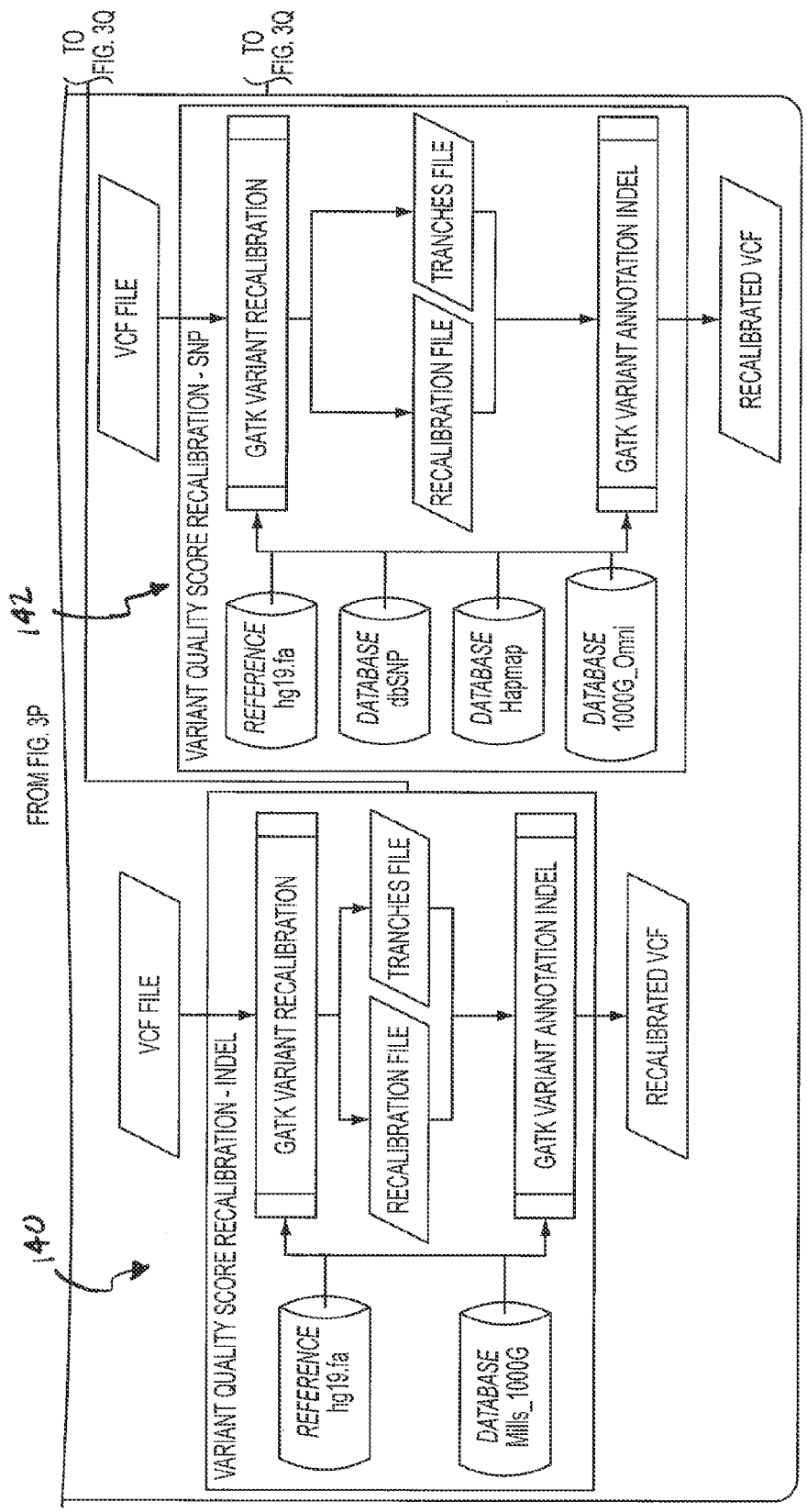
FIG. 3P is a portion of the parallelized work-flow diagram below and to the left of the portion set forth in FIG. 3Q.
Figure 3Q:
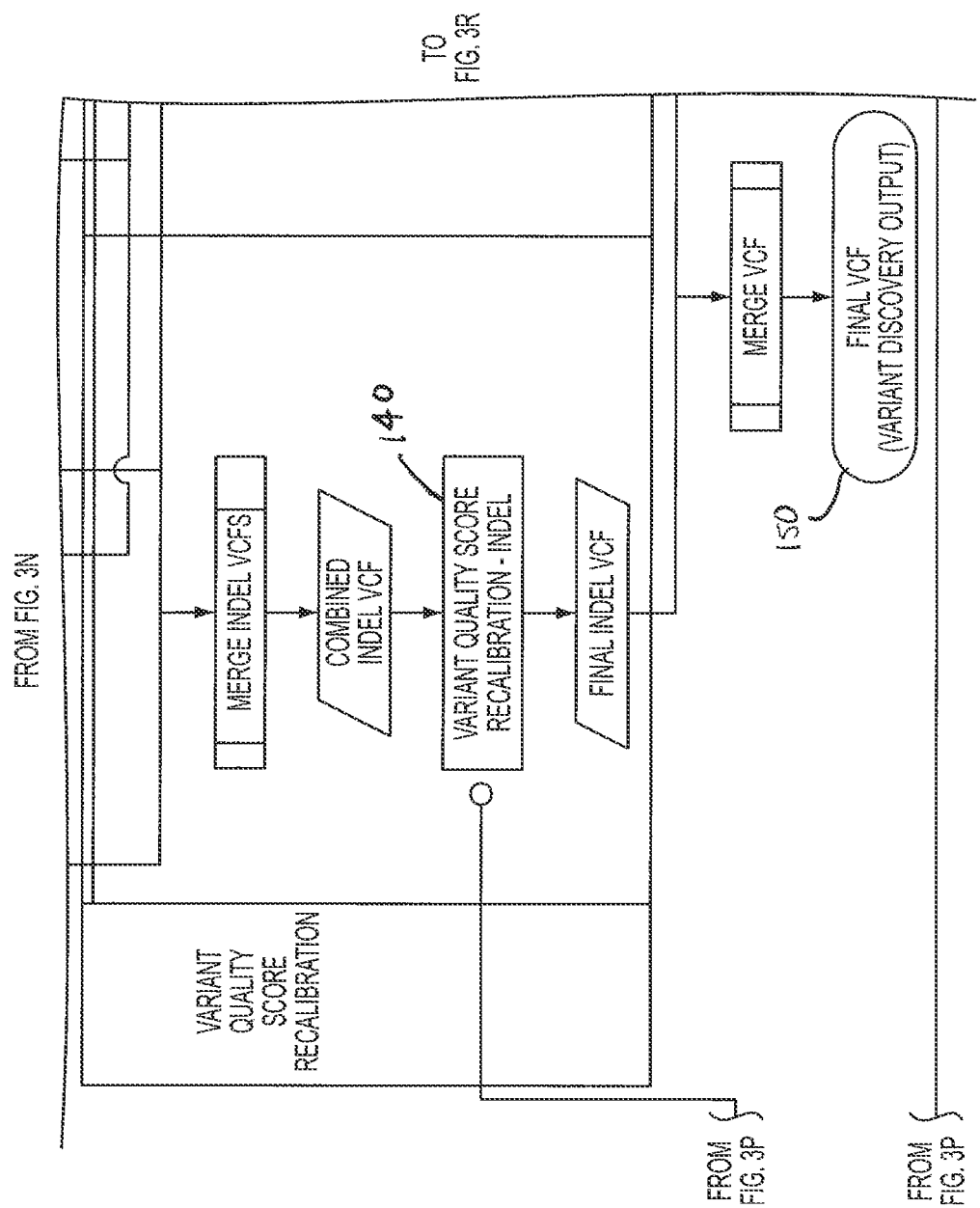
FIG. 3Q is a portion of the parallelized work-flow diagram to the right of the portion set forth in FIG. 3P, to the left of the portion set forth in FIG. 3R, and below the portion set forth in FIG. 3N.
Figure 3R:
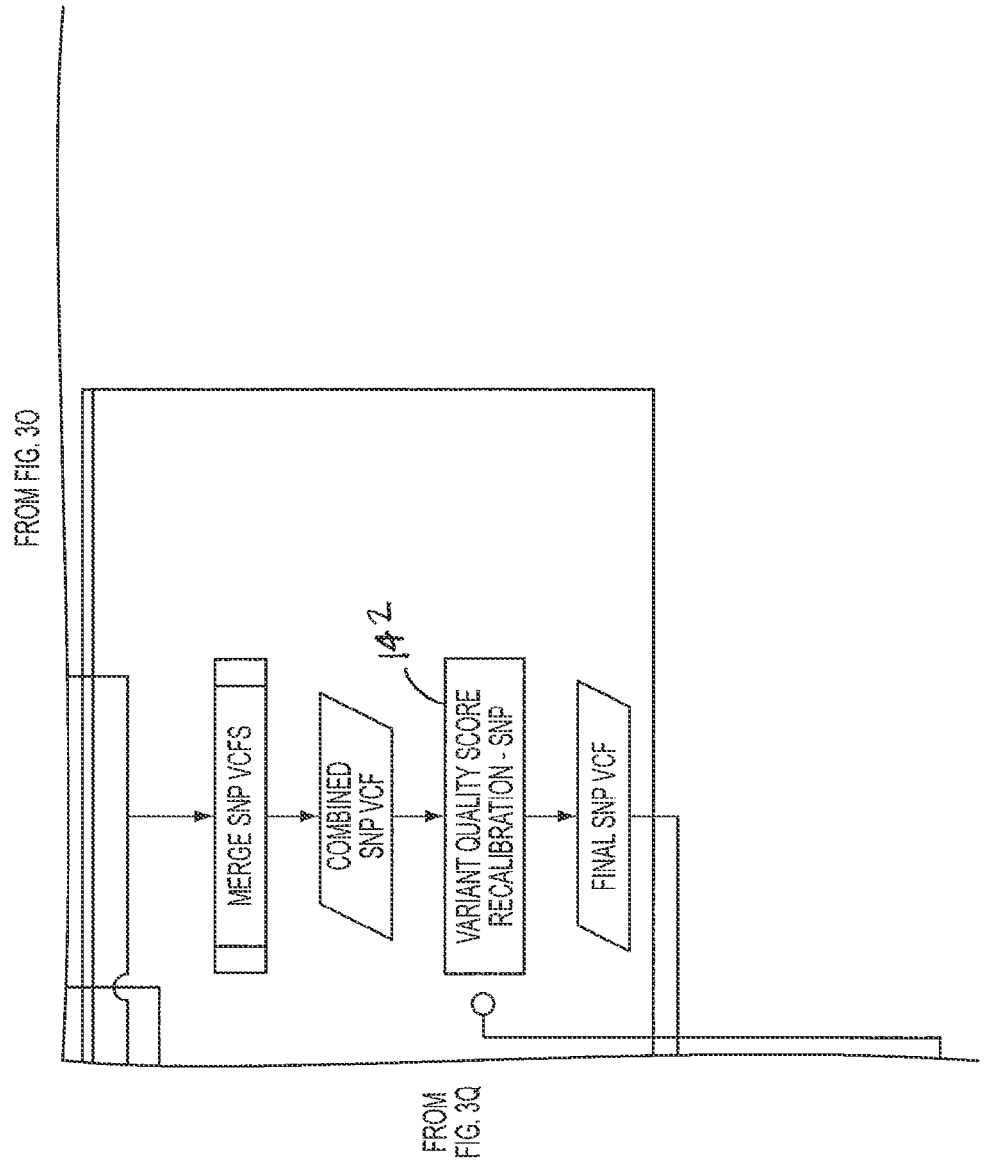

Churchill implementation. A schematic representation of an another embodiment (referred to as "Churchill") is shown in FIGS. 3A-3R. Churchill may be implemented as a mixture of Bash and Python scripts, linking and preparing for parallelization the inputs and outputs of BWA, Picard, SAMTools, and GATK. A single, simple configuration file may allow the user to specify environmental variables, the location of the input FASTQ files, the output project directory, reference files, annotation databases, sample-specific parameters, and other important settings. Churchill may be initialized and executed using a single python script, 'churchill.py', and a Cython-compiled C library. Churchill may begin by creating the scripts required to run the entire pipeline and then proceeds to execute (or submit to the job scheduler) the scripts in desired parallelization method (shared memory, GNU make, SGE, or PBS) specified by the user in an argument to 'churchill.py'.

Different ways to create new tasks and implement parallelization of these tasks in the Linux environment were investigated. To ensure that Churchill would be of utility to the widest number of researchers, the pipeline was developed such that it could be executed with three of the most commonly utilized environments for distributed computing (Table S1).

1. Xargs. The presence of dependencies among sub tasks makes it straightforward to spawn multiple processes using the xargs utility. Originally developed as a tool to build and execute command lines from standard input, xargs can also be used to run multiple command lines, essentially maintaining a simple task pool. Because xargs does not return until all lines of the task file are run, task synchronization is handled implicitly. Alternatives to xargs, such as GNU parallel, can also be used as the task dispatcher. However, xargs was chosen because it is typically available in all Unix-like systems, while GNU parallel generally requires separate installation.

2. GNU Make. GNU Make specializes in describing the interdependencies among tasks and can also be used to control the proper ordering and the running of the sub tasks. Dependencies are maintained in the Makefile(s) through the use of sentinel files.

3. Qsub (in a Distributed Cluster Environment). Parallelization with xargs is simple but limited by the fact that it will only work in a shared memory environment. In a distributed cluster environment, tasks are usually created by submitting jobs to job queues and their executions managed by a job scheduler. The Sun Grid Engine (SGE), and the Portable Batch System (PBS/TORQUE), for example, both provide the "qsub" command for such purpose. In order to adapt the Churchill pipeline for execution in these environments, the scripts for task creation were modified to maintain task dependency as jobs are submitted. Dependencies are maintained in both environments by job ID numbers.

4. Distributed Make. Distmake is a distributed, parallel, GNU Make-compatible program that can be used in both PBS and SGE to process a standard Makefile. Therefore, parallelization using GNU Make represents a generic way to work across multiple platforms.

5. Hadoop

The MapReduce framework has been popularized by the success of search engines such as Google and Yahoo, and has been used in bioinformatics. Compared with traditional HPC clusters as described in the previous section, MapReduce employees a distributed file system instead of the centralized storage system. MapReduce framework is able to take advantage of data locality and is also fault-tolerant. The described pipeline workflow is readily dividable into different Map and Reduce stages and fits well in this framework.

A comparison grid of parallelization environments vs. parallelization methods (Table S1)

| Parallelization method | Parallelization environment | | | |
|---|---|---|---|---|
| | Shared memory | PBS | SGE | Hadoop |
| Xargs | Yes | No | No | No |
| GNU Make | Yes | Yes (via distmake) | Yes (via qmake/distmake) | No |
| Qsub | No | Yes | Yes | No |
| MapReduce | No | No | No | Yes |

Ease of Implementation

Among all parallelization environments, shared-memory parallelism may be the simplest to program, since all processes have access to all resources. However, for embarrassingly parallel problems like NGS data processing, where there is little inter-process communication required, distributed parallelism may be straightforward to implement as well. An important step may be the identification of sub-task dependencies, and then tasks can be submitted using different mechanisms/job schedulers.

Ease of Deployment

Shared-memory solution again has an advantage in deployment: there is only one server to set up and configure, as opposed to multiple nodes in distributed environment. However, when the storage is provided by network attached device via NFS protocol, it is relatively easy to saturate the single mount point to reach the limitation of NFS. In this case faster network with lower latency should be used.

Fault Tolerance

In case one core fails in a shared-memory server, the OS is usually able to detect this and mark it as unusable, and the task that has already been assigned to the core will be moved to another healthy core. However, this may not be true if the thread affinity has been set, pinning that task to run on a particular core. On the other hand, if a node fails in an HPC cluster, the job scheduler may or may not be able/configured to detect the failure in time and then subsequently reschedule the involved task to another healthy node; as a consequence the entire pipeline will come to a halt in this case. This is not a problem for the MapReduce framework, owing to its built-in fault tolerance capacity.

Costs and Maintenance Issues

The popularity of multi-core processors is largely due to the decreasing costs to manufacture more cores in a chip. Compared to a multi-node cluster, shared-memory server also takes less space, used less electricity for power and cooling, and usually easier to maintain.

Availability of HPC Environments

Shared-memory servers are generally for dedicated use, while HPC clusters are usually shared by many users. In a cluster environment, jobs submitted are queued until resources become available. It is also not uncommon that the user is required to estimate the time necessary to run the job and submit that information along with the job itself; when the specified time is exceeded the job will be prematurely terminated. For these reasons, shared-memory server is a better choice for usages that require high availability. Clusters running Hadoop are often available on a pay-per-use basis as commercial cloud computing services, providing an alternative to fully dedicated and fully shared HPC environments.

Scalability

A limitation of shared-memory server is its inability to scale beyond the number of cores on board, which is not an issue with HPC clusters or Hadoop clusters. This problem can be addressed by combining multiple levels of parallelism: a cluster can be built with multiple nodes, each of which is a many-core shared-memory server.

Limitations of Parallelization by GNU Make

GNU Make was originally designed for building projects with multiple dependencies; its capacity to execute multiple commands simultaneous was a nice side effect. There are, however, several limitations. For example, stdout and stderr are shared by all sub processes and special care is needed to redirect individual process' message to separate log files. The sharing of stdin is a much more severe problem, because any program relying on receiving input from stdin will not work correctly. Other limitations include the inability of Makefile to describe iterative or dynamic processes, and no additional information about different jobs (e.g., expected run time) can be used to help with job scheduling and better load balancing. Despite these shortcomings, we believe GNU Make is still the preferred way to parallelize NGS data analysis workflow for current computing environments.

Cost Reduction

The above pipeline works well on commodity computer hardware. On the other hand, the shared memory server is less scalable than clusters. To overcome this, distributed computing environment was deployed in which the 48-core server is one of the "super" nodes. This configuration may provide solution to the increasing demands for computational resources for many small sequencing cores or labs with one or two HiSeq.

Segmented Parallelized Workflow

Referring primarily to FIGS. 3A-3R, in an embodiment, the above pipeline may be further enhanced by a segmented workflow that extends beyond the chromosome centric approach. An enhanced pipeline may utilize an approach that evenly subdivides the whole human genome into multiple regions with fixed boundaries (subregions, 0, 1, . . . M) 104, enabling a load balanced and independent execution of the local realignment, deduplication, recalibration and genotyping steps (See, also, FIG. 5B). In theory, the extremely large size of the human genome (~3 billion base pairs) enables achievement of near-embarrassingly parallel execution of these steps. For example, dividing the genome into 3,000,000 base pair chromosomal subregions enables execution of these steps in 1,000 parallel processes. The number of subregions created by this embodiment can be specified by the user, although increasing this variable to twice the number of cores available for processing may lead to improved load balancing. In order to ensure proper processing of regional boundaries, at both ends of each region a 3 kilobase overlap of the adjacent region may be included. This overlap acts as a "buffer zone" to provide appropriate detection of variants near or spanning region boundaries, as is possible, for instance, in the case of insertions and deletions (indels). The resulting region and overlap boundary information may be saved in the GATK intervals file format.

Figure 5A:
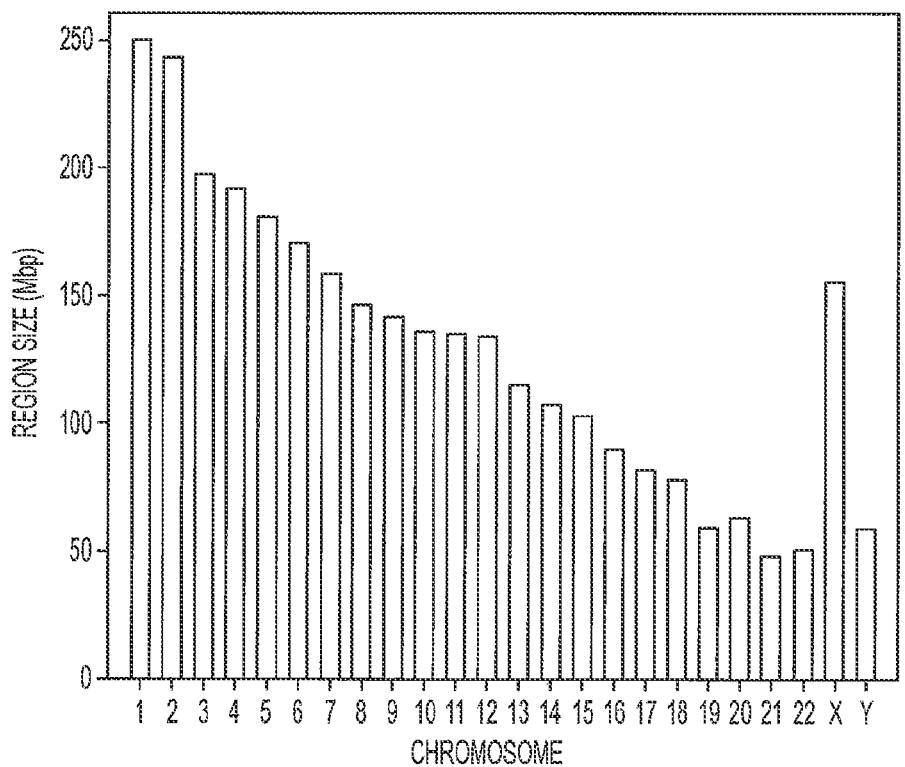
FIGS. 5A-5B provide parallel processing region size comparisons between the embodiments which break according to chromosomes versus embodiments which can break chromosomes into smaller regions.
Figure 5B:
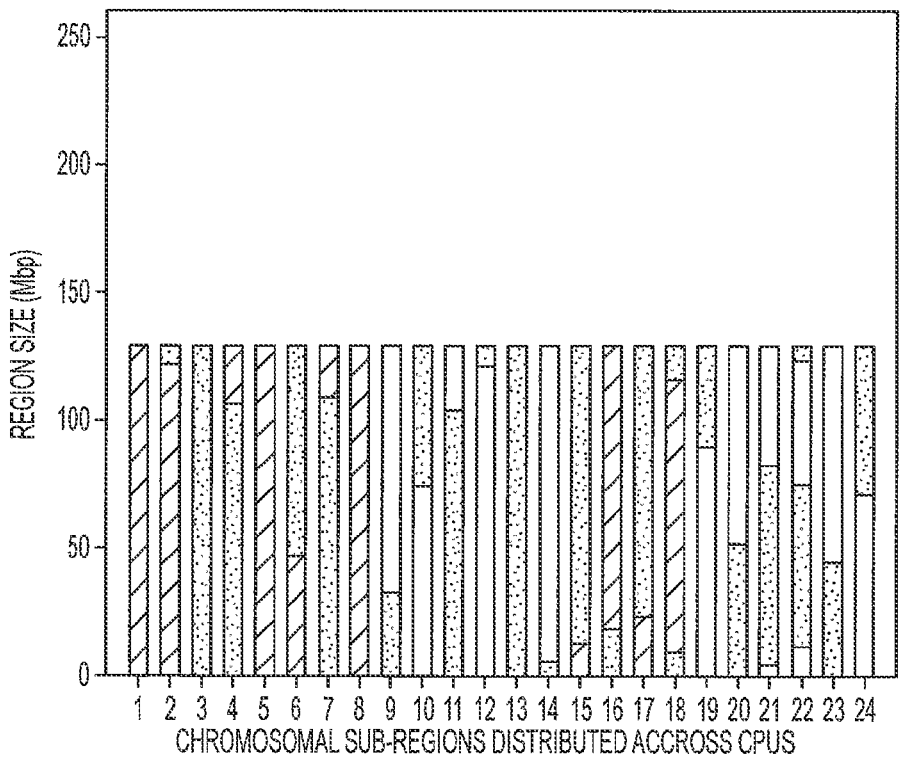

As shown in FIGS. 5A and 5B, parallelization by chromosome may include an inherent load imbalance, due to the varying sizes of the human chromosomes (FIG. 5A). However, utilization of chromosomal subregions enables equilibration of the analysis load across all available processors (FIG. 5B).

The post-alignment steps of the analysis process (local realignment, duplicate read removal, base quality score recalibration, genotyping and variant quality score recalibration) may not simply be performed on these subregions without refinement of each step to achieve high levels of parallelization without sacrificing data integrity and quality.

Steps of the current workflow and the optimization, with reference to FIGS. 3A-3R are detailed below:

Parallelized Alignment to a Reference Sequence.

Figure 6:
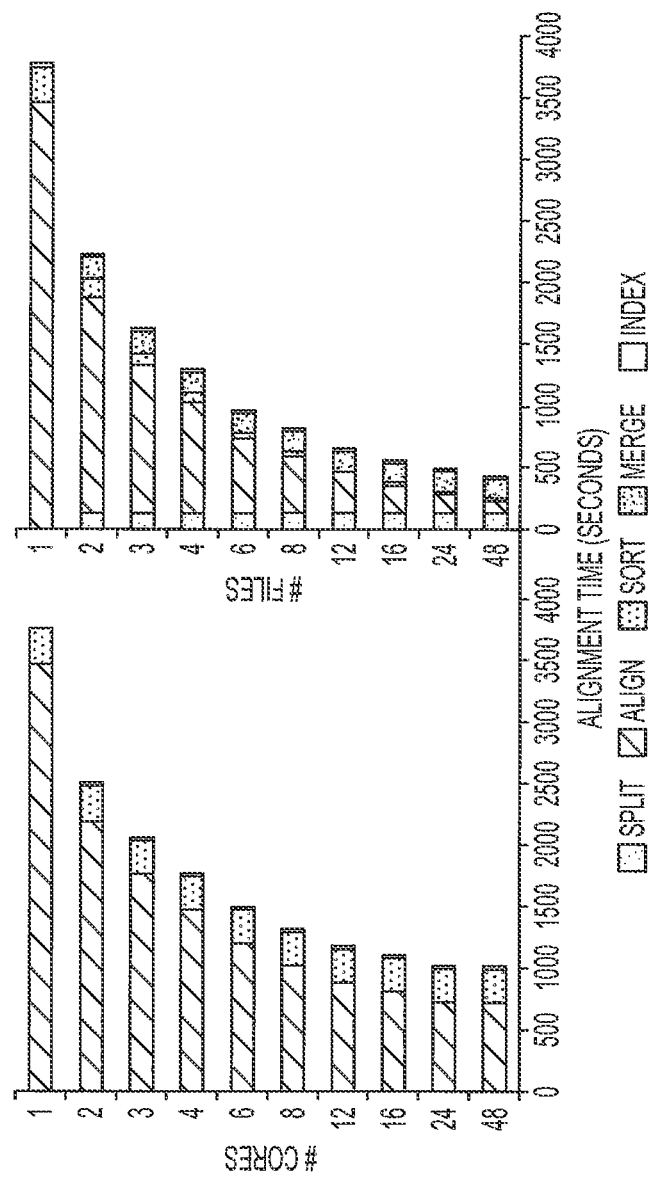
FIG. 6 provides comparison graphs of the parallel processing approach of disclosed embodiments versus other parallel processing approaches.

For the initial alignment step, BWA is utilized to perform reference genome alignment 100 with the reads contained in paired FASTQ files. The speed of the process can be increased through utilization of inbuilt multithreading capabilities of the alignment algorithm by executing the aligner in multithreading mode (for example, using the bwa aln -t option to specify the number of threads). However, implementation of alignment within the current pipeline utilizes an approach whereby the total raw input sequencing data (typically 400-800 million paired reads) is split into multiple smaller FASTQ files and aligned using multiple single-threaded parallel instances of the alignment algorithm. The number of paired-end FASTQ files generated during the sequencing run is controlled by the—fastq-cluster-count parameter of Illumnina's BCL-conversion process (CASAVA 1.8.2), which specifies the maximum number of reads per output FASTQ file. The default value of 4,000,000 works well with the current pipeline. However, decreasing the number of reads per FASTQ to 1,000,000 may result in increased alignment speed due to better load balancing. In adopting this approach, the current pipeline may overcome inefficiencies of in-built multithreading within the alignment algorithm. For example, in the case of BWA, the current implementation of alignment reduces alignment time by ~60% (See FIG. 6). The modest overhead of splitting the original FASTQ file and merging the resulting alignments was far outweighed by the reduction in the alignment and sorting time that resulted from this approach. Parallelized alignment (FIG. 6A, right) using 48 input files with 48 CPUs was 9 times faster than single-threaded BWA and 2.4 times faster than multi-threaded BWA (FIG. 6B, left).

Parallelized Generation of Subregional BAMs.

Figure 4:
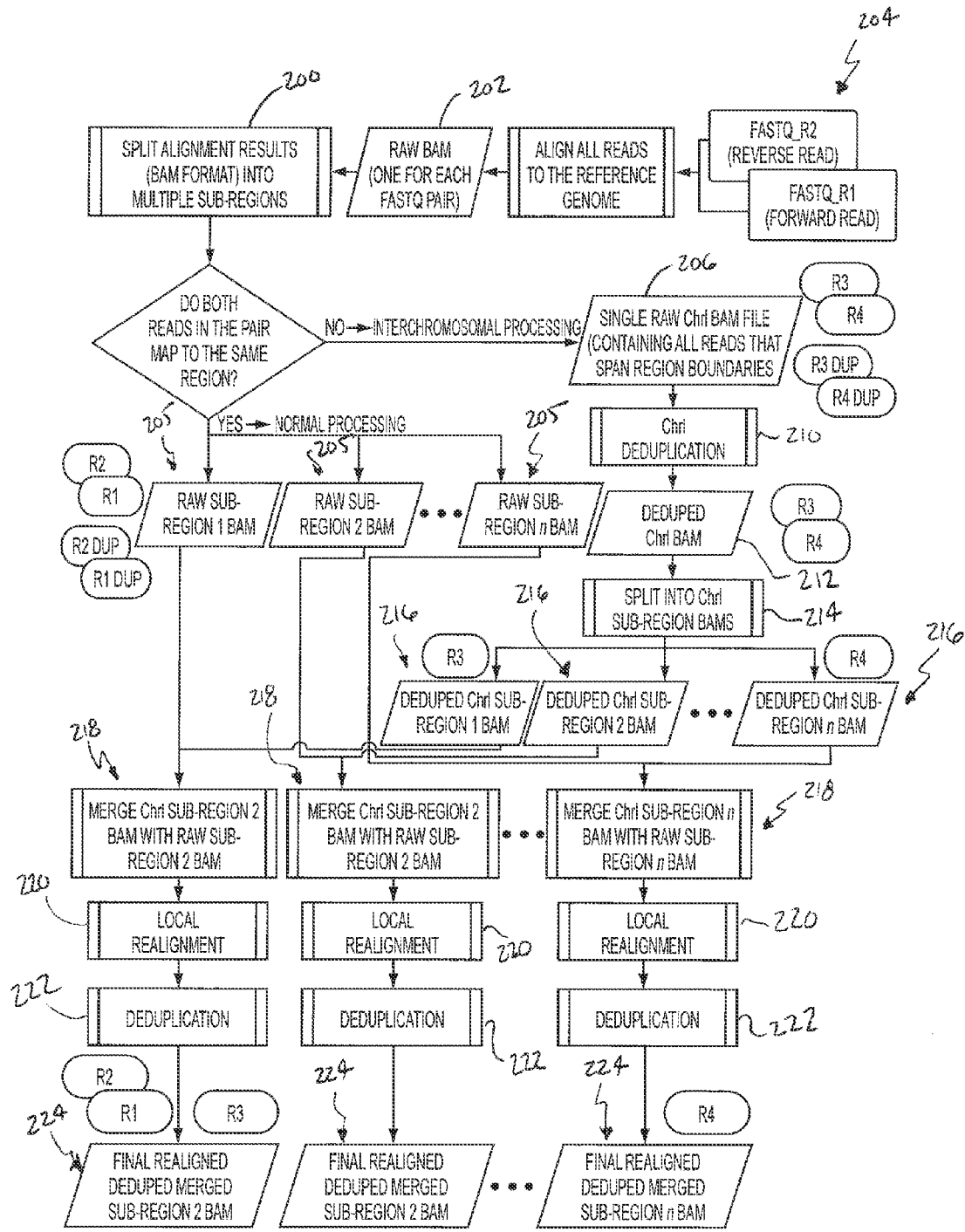
FIG. 4 provides a specific representation of the parallelized work flow that enables parallelization of the deduplication process without sacrificing data quality according to FIG. 3.

As shown in FIGS. 3B-3E and FIG. 4, following alignment, reads are split into multiple subregion BAM files. If both reads in the pair map to the same region they are placed into the appropriate subregion BAM file 104. Otherwise, the reads are placed in the interchromosomal (ChrI) BAM file 106. Once the raw aligned reads have been processed, the interchromosomal reads can then be correctly deduplicated. The deduplicated interchromosomal reads are individually merged back into their appropriate subregion BAM. These merged subregion BAMs then undergo local realignment and deduplication, creating deduplicated subregion BAMs ready for the recalibration and genotyping steps. At the heart of the current pipeline is an algorithm developed to convert the raw BAM files produced during alignment into subregions, enabling the parallel implementation of all of the subsequent analysis steps As shown in FIG. 4, this approach may include the following steps:

1. Split raw BAM by region. In step 200, the genome is split into M chromosomal subregions 104, where the value of M is defined by the desired level of parallelization. Utilization of the current parallelized alignment approach generates N raw BAM files (derived from alignment of N pairs of input FASTQ files 204 to the entire genome) 202. These BAM files are split in step 200 according to the coordinates of the subregions, yielding M×N split BAM files 205. Read pairs in which mates map to different subregions are temporarily transferred to separate split BAM files, one for each of the N input BAM files, identified as chrI.bam ("I" is short for interchromosomal mapping) 106.

2. Merge split BAMs by subregion. For each of the genomic subregions, the N split BAM files corresponding to a given subregion are merged into M subregional BAM files 208 (see also FIGS. 3H and 3I), each containing all of the read pairs mapped within the boundaries of that subregion.

3. Merge split chrI BAMs. The N chrI BAM files 106 are merged into a single genome-wide interchromosomal BAM file 206 (see also FIG. 3I).

4. Deduplicate chrI. Merging all inter-subregional read pairs (including reads that may later be used to identify interchromosomal translocations) into a single chrI BAM file enables appropriate duplicate read removal (deduplication) in step 210. Picard Tools MarkDuplicates may be used to process the chrI BAM, yielding a deduplicated chrI BAM file 212. See, also, FIG. 3I.

5. Merge chrI reads with subregional BAMs. The deduplicated interchromosomal paired reads are split according to subregion in step 214 to produce deduplicated subregional chrI BAM files 216 (see, also, FIG. 3I), and the individual reads are merged back into the appropriate subregion BAM in step 218 according to the reads coordinates (see, also, FIGS. 3H and 3I). Steps of local realignment 220 and deduplication 222 may be then performed in parallel on each of the sub-regional BAM files (see, also, FIGS. 3H-3L). The resulting alignment files 224 contain both appropriately deduplicated interchromosomal and regular reads, thereby enabling parallelization of the full deduplication process later in the analysis process.

The final output of this step is multiple BAM files 224, one for every genomic subregion, which include appropriately mapped and deduplicated interchromosomal reads, thereby enabling parallelization of the subsequent steps such as local realignment.

Parallelized Local Realignment Around Indels.

The current algorithm enables high levels of parallelization of the post-alignment processing steps to produce analysis ready reads. In the first step, local read realignment is performed to correct for potential alignment errors around indels. Mapping of reads around the edges of indels often results in misaligned bases creating false positive SNP calls. Local realignment uses these mismatching bases to determine if a site should be realigned, and may apply a computationally intensive Smith-Waterman algorithm to determine the most consistent placement of the reads with respect to the indel and remove misalignment artifacts (see, Smith, T. F. & Waterman, M. S. Identification of common molecular subsequences. J Mol Biol 147, 195-197 (1981), the disclosure of which is incorporated by reference). An advantage of the current embodiment in parallelizing local realignment 220 is that all reads from a given sample may be used to perform the local realignment, ensuring the greatest possible accuracy and improving novel indel detection. Moreover, applying sample level local realignment across the current embodiment's subregions results in significant improvements in speed.

Parallelized Duplicate Read Removal.

The second post-alignment processing step identifies duplicate reads and removes sequencing artifacts coming from PCR amplification errors introduced during preparation of the DNA sample in the laboratory. Reads containing amplification errors may be represented in artificially high numbers and, as such, failure to remove these reads from the data set may have a significant negative effect on the final result by introducing variants that reflect these errors rather than true biological polymorphisms. The deduplication process 222 identifies read pairs with identical external coordinates and subsequently reduces the data set to include only one copy of the duplicate sequence with highest mapping quality. Picard Tools MarkDuplicates is the tool most commonly utilized to identify duplicate reads both within and between chromosomes (http://picard.sourceforge.net). Current best practices require that the deduplication process be performed using a single BAM file, containing all of the reads from the sequencing run. This is the approach utilized by the GATK-QUEUE analysis pipeline. However, in addition to this prolonged serial deduplication, the process of merging the BAM files into a single file cannot be parallelized. These processes result in lengthy single-threaded computations that substantially increase analysis run time. The current algorithm overcomes this significant limitation by keeping interchromosomal reads together initially and deduplicating them as part of the raw BAM split and merge processes (As discussed above). This step happens before the individual reads in the pair are merged by coordinates into the appropriate subregional BAMs. This innovative approach ensures proper deduplication of these interchromosomal reads and enables safe parallelization of the remainder of the deduplication process across both chromosomes and chromosomal subregions. In this way it is possible to achieve high levels of parallelization of the duplicate marking and removal process without compromising data integrity. The current deduplicated BAM is indistinguishable from the results obtained from the lengthy process of post-alignment processing of a single merged genome-wide BAM file.

Parallelization of Base Quality Score Recalibration.

Each base of each read has an associated quality score, corresponding to the probability of a sequencing error. The reported quality scores are known to be inaccurate and as such must be recalibrated prior to genotyping, where they are used in the Bayesian genotype likelihood model employed by GATK's UnifiedGenotyper (Depristo, 2011). After recalibration, the recalibrated quality scores in the output BAM will more closely correspond to the probability of a sequencing error. Moreover, the recalibration tool corrects for variation in quality with respect to machine cycle and sequence context, thus producing both more accurate and widely dispersed quality scores. Churchill uses GATK's base quality score recalibration (BQSR) algorithm 120 (see, also, FIGS. 3J, 3K and 3L), which analyzes covariation among several features of a base including the reported quality score, the position within the read and the preceding and current nucleotide (sequencing chemistry effect). These covariates are then applied through a piecewise tabular correction 122 (see, also, FIGS. 3J, 3N and 3O) to recalibrate the quality scores of all reads in a given BAM file. However, according to the Broad's best practices, BQSR requires a pool of all covariates from across the genome for proper calculation. Therefore, to ensure integrity of the recalibration process, the current embodiment merges the covariate results for each subregion 124 (see, also, FIG. 3K) so that each parallel recalibration instance has input data from the entire genome rather than just its region. The benefit of this approach is that it enables the current embodiment to use the entire dataset for recalibration purposes, improving accuracy and avoiding down-sampling which will lead to non-determinism.

Parallelization of Variant Calling.

In the penultimate step of the current analysis process, variant calls are generated with GATK Unified Genotyper (UG) 130 using the analysis ready reads generated during recalibration. UG uses a Bayesian genotype likelihood model to simultaneously estimate population allele frequency and the most likely genotypes of each sample (Depristo, 2011). The current embodiment is capable of implementing UG on both single sample data and multi-sample data, where variant information from all samples in a given experiment is utilized to improve genotyping accuracy. Due to the overlapping buffer zones at the ends of each region, it is possible that a variant occurring in one of these zones may be called twice: once in the region to which it belongs and once in the overlap zone of the adjacent region (see FIG. 7). This is corrected by assigning the variant to the appropriate subregion and removing its buffer-zone duplicate from the final merged raw variants file. This determination is made based on the location of the variant call and its position relative to the fixed subregion boundaries. The raw genotype calls from each subregion are concatenated into genome-wide VCF files for both SNPs 132 and indels 134 (See, also, FIGS. 3M, 3N and 3O). Unlike BQSR, variant quality score recalibration (VQSR) 140/142 may be performed using all variants, in a non-parallel mode, to ensure appropriate recalibration calculations. However, this final step is relatively fast and a lack of parallelization does not appreciably slow down the analysis. The final output from the current analysis pipeline is a recalibrated VCF 150, ready for down-stream analysis and interpretation (See, also, FIGS. 3P-3R).

Figure 7:
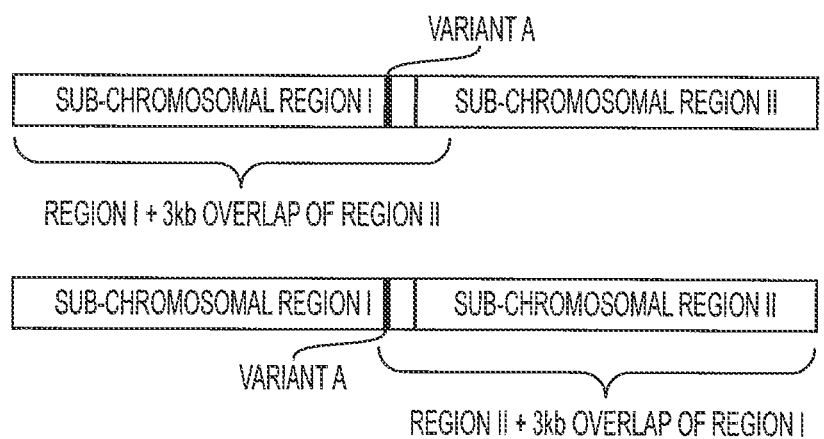
FIG. 7 is an illustration of subregion processing according to the embodiment of FIGS. 3 and 4.

FIG. 7, introduced above, illustrates subregion processing as discussed herein. Chromosomes are split into subregions for the processes of realignment, duplicate removal, base quality score recalibration, and genotyping. If duplicate genotyping calls are made in the overlapping regions, the current embodiment assigns the variant to the correct subregion. These buffer zones allow data integrity to be maintained while enabling parallelization of the data processing steps. For example, Variant A called in the last 3 kilobases of Region I is called twice, once in the processing of Region I, once in the processing of Region II; it is assigned to Region I.

Comparison of Parallelization Strategies Used by GATK-Queue, HugeSeq, and the Current Embodiment.

Each pipeline attempts to parallelize the workflow in order to reduce the time required to produce VCF results from FASTQ input files. To ensure appropriate read deduplication and recalibration, GATK-Queue's strategy is to perform two costly merge processes. First, multiple realigned BAM files are merged into a single file to perform deduplication. Then second, after calculating covariates across the entire genome, recalibration is applied across intervals, and the resulting recalibrated BAM files are then merged prior to the genotyping steps. As the merge BAM process is not parallelized, these two steps are computationally inefficient and substantially slow down GATK-Queue's analysis process.

HugeSeq's approach is to skip the merge process, and apply all subsequent steps on a strictly per-chromosome level (see, Lam, H. Y. et al. Detecting and annotating genetic variations using the HugeSeq pipeline. Nat Biotechnol 30, 226-229 (2012)). While this results in a significant reduction in processing time, data integrity is sacrificed for speed, as at several points HugeSeq deviates from widely accepted best practice. For example, covariates are calculated across each chromosome separately during HugeSeq's recalibration step, while GATK's best practice highly recommends that covariates are calculated across the entire genome. Secondly, during deduplication, any read pairs that are considered interchromosomal are split up and assigned to their respective chromosomes. This split prevents any interchromosomal reads from being properly deduplicated, as the position of both the reads in a pair are required to verify two reads are duplicates of each other. These reads are simply ignored by the deduplication process, leading to a substantial reduction in data quality. The authors of HugeSeq recognized this limitation of their approach, stating that parallelization of interchromosomal read detection process was not possible[6]. However, reads with mates mapped to different chromosomes provide important information about possible interchromosomal rearrangement (translocations) and should not be simply ignored. For example, according to the July 2012 release of the Catalogue of Somatic Mutations in Cancer (COSMIC v60), there are currently over 8000 gene fusions known to be associated with benign and malignant tumors, many of which have been shown to play key roles in cancer initiation (See, Forbes, S. A. et al. COSMIC (the Catalogue of Somatic Mutations in Cancer): a resource to investigate acquired mutations in human cancer. Nucleic Acids Res 38, D652-657 (2010)). The clinical relevance of interchromosomal reads is highlighted by the fact that gene fusions can be linked to clinical outcomes; for example, the presence of the BCR-ABL1 fusion is a powerful predictor of clinical outcome in both pediatric (see, Collins-Underwood, J. R. & Mullighan, C. G. Genomic profiling of high-risk acute lymphoblastic leukemia. Leukemia 24, 1676-1685 (2010)), and adult leukemias (see, Marin, D. et al. Assessment of BCR-ABL1 transcript levels at 3 months is the only requirement for predicting outcome for patients with chronic myeloid leukemia treated with tyrosine kinase inhibitors. J Clin Oncol 30, 232-238 (2012)).

In contrast, the current approach achieves both substantial increases in processing speed and maintains data integrity by not deviating from best practices. For example, interchromosomal read pairs are kept together during the deduplication process, so that duplicates may be properly identified. Covariates are counted across smaller subregions, but results are then merged into a genome-wide covariates list before being applied back to the chromosomal subregions. Finally, current embodiments's "buffer zone" and variant merging algorithm ensures appropriate processing of variants near or spanning subregion boundaries (as is possible in the case of indels). As a result, the current embodiment achieves results that are both identical to the serial analysis approach and 100% deterministic regardless of the level of parallelization implemented to speed up the analysis process.

As shown in FIG. 6, BWA alignment was performed using 4,000,000 paired 100 bp Illumina HiSeq 2000 reads using the human reference genome (hg19). In the standard single-threaded approach, alignment was completed in ~3,900 seconds (top bar, both panels). (A). Alignment time using BWAs in-built parallelization using increasing degrees of multithreading. Utilization of 48 parallel threads (bwa aln -t 48) enabled alignment to be completed in ~1140 seconds (bottom bar). (B). Alignment time using the Churchill approach using the same input data. The input FASTQ file was split into multiple input files and analyzed in parallel as single-threaded independent processes (e.g. 2 pairs of files each with 2,000,000 reads each analyzed simultaneously with a total of 2 CPUs). Churchill parallelized alignment using 48 input files with 48 CPUs was completed in ~420 seconds (9 times faster than single-threaded BWA and 2.4 times faster than multi-threaded BWA). Data shown is representative of three separate experiments.

Schematic Representation of Current Embodiment.

A schematic representation of the entire current exemplary embodiment's process is shown in FIGS. 3A-3R. The current process may be implemented as a mixture of Bash and Python scripts, linking and preparing for parallelization the inputs and outputs of BWA, Picard, SAMTools, and GATK. A single, simple configuration file allows the user to specify environmental variables, the location of the input FASTQ files, the output project directory, reference files, annotation databases, sample-specific parameters, and other important settings. The current embodiment is initialized and executed using a single python script, 'churchill.py', and a Cython-compiled C library. The current embodiment begins by creating the scripts required to run the entire pipeline and then proceeds to execute (or submit to the job scheduler) the scripts in desired parallelization method (shared memory, GNU make, SGE, or PBS) specified by the user in an argument to 'churchill.py'.

Testing and Test Data

To test the above described parallel pipeline, sequence data was generated by the Illumina HiSeq 2000 in the Biomedical Genomics Core, The Research Institute at The Nationwide Children's Hospital was used, including but not limited to Illumina HiSeq 2000 2×100 bp paired-end whole genome sequencing data sets with 30× average coverage. The pipeline was also run on the publicly available data to test its performance on both whole genome and whole exome sequencing data.

Profiling, and Benchmarking

In addition to measuring the running time, the load average and memory usage for the whole system was recorded. A cron job was created that extracted the relevant information from /proc/loadavg and /proc/meminfo at specified interval (10 seconds in our experiments) so the entire CPU and Memory usage pattern were logged. Graphs were tabulated and plotted based on the logs. The current embodiment (Churchill) was not only significantly faster than alternative approaches, but also demonstrated highly efficient utilization of compute resources.

Figure 8:
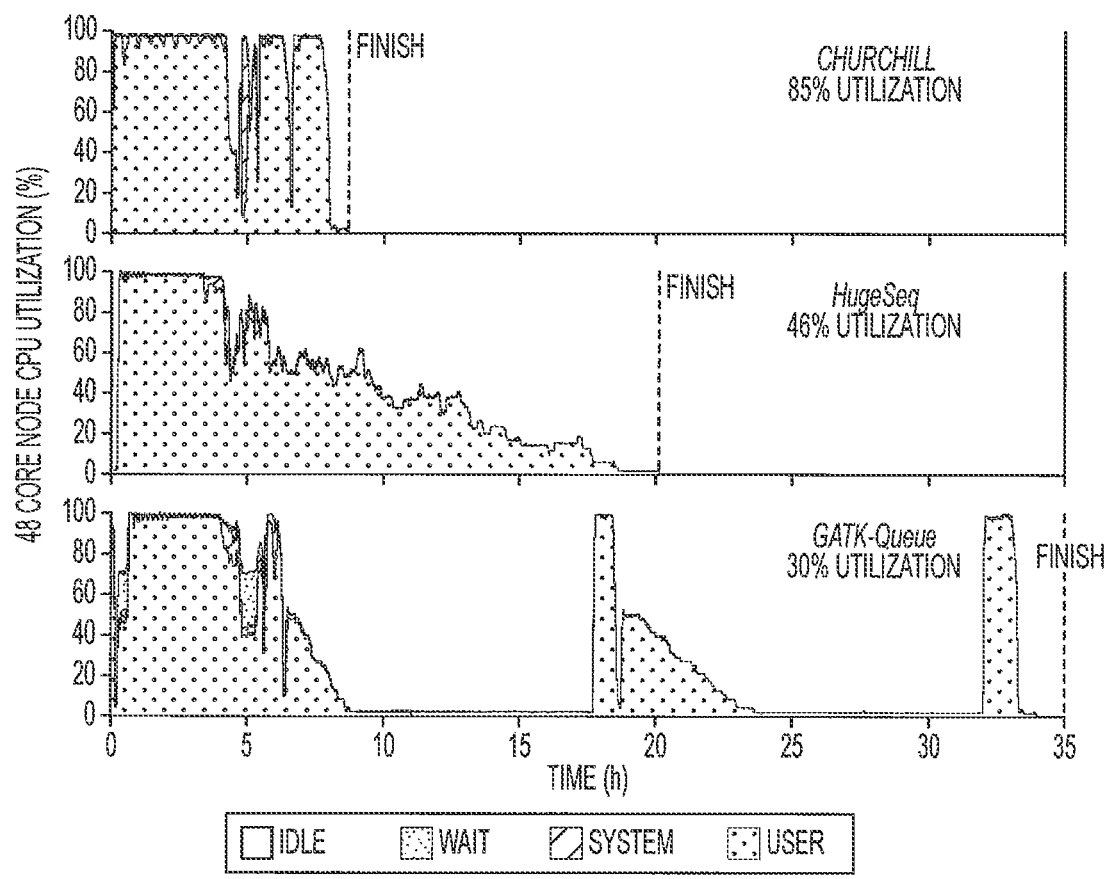
FIG. 8 is a comparison of a current embodiment's performance versus other known secondary analysis approaches.

As shown in FIG. 8, utilizing a single server (Dell R815), Churchill is roughly 2× faster than HugeSeq, 4× faster than GATK-Queue, and 10× faster than a naïve serial implementation with in-built multithreading enabled.

Figure 9:
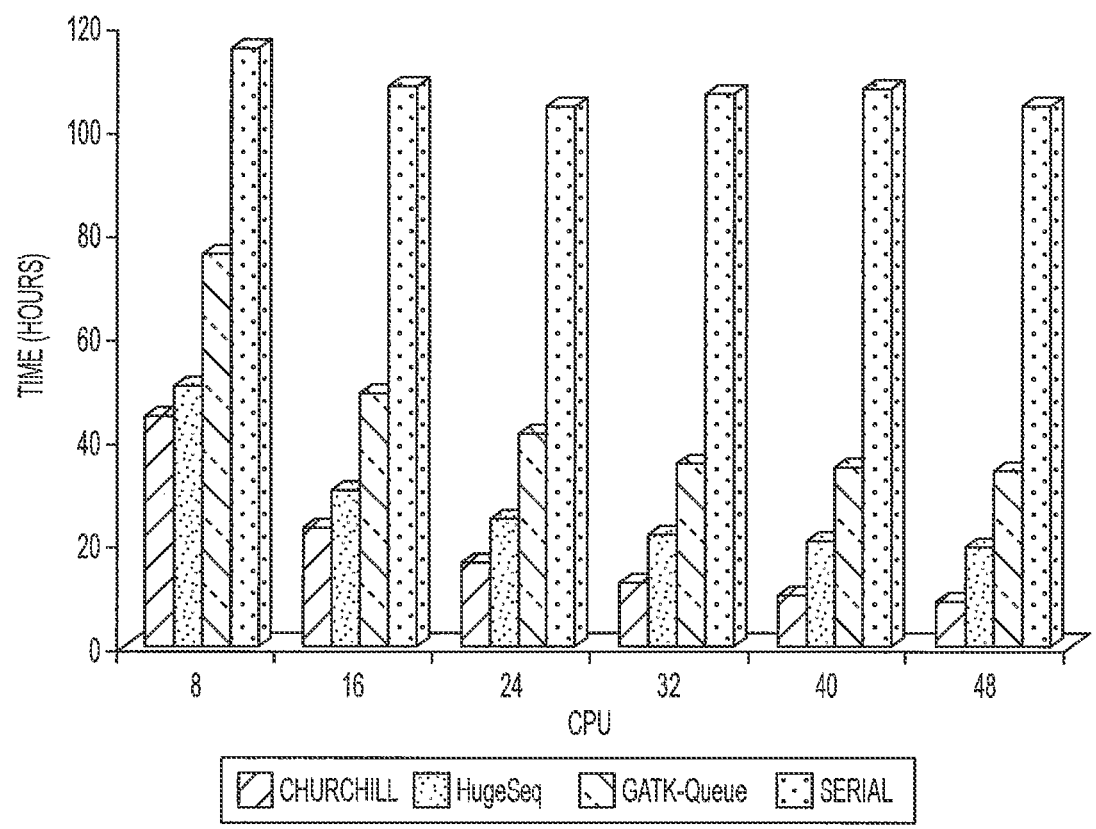
FIG. 9 is a comparison of a current embodiment's performance versus other known secondary analysis approaches using increasing numbers of CPU cores.
Figure 10:
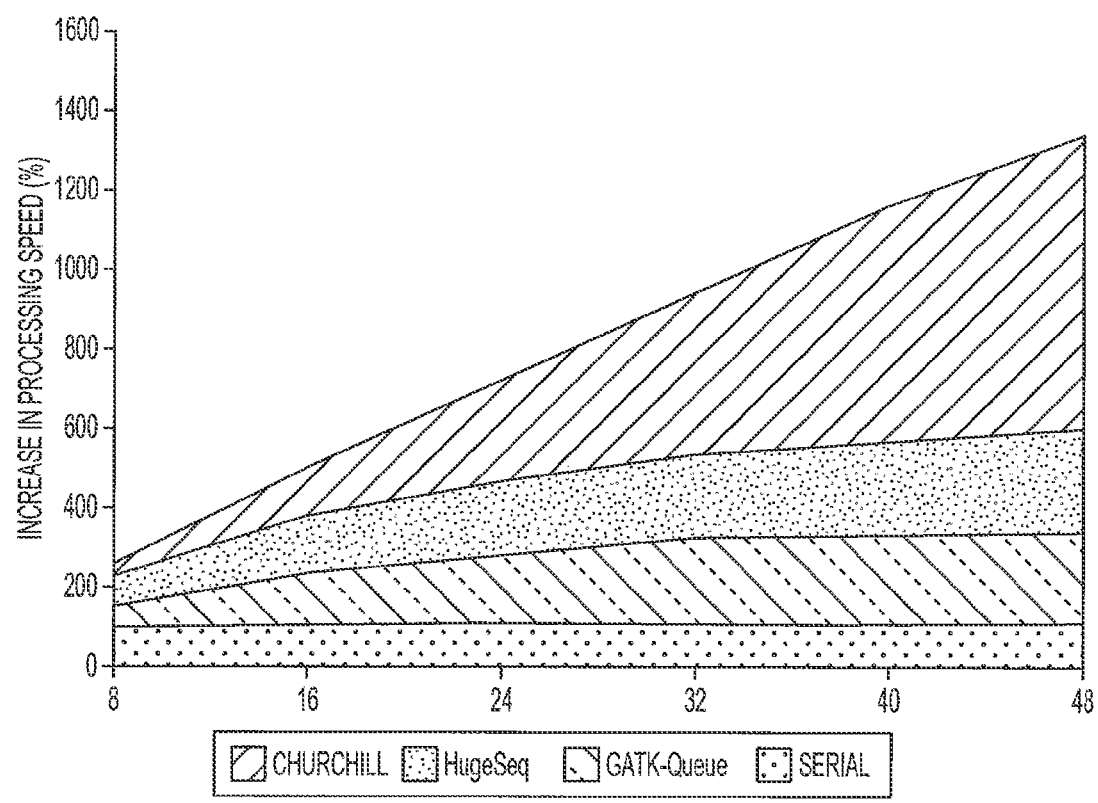
FIG. 10 is a comparison of current embodiment's performance versus other known secondary analysis approaches using increasing numbers of CPU cores.

As shown in FIGS. 9 and 10, Churchill scales much better than the alternatives; the speed differential between Churchill and alternatives increases as more cores in a given compute node are used.

Significant Speed Improvement

Figure 11:
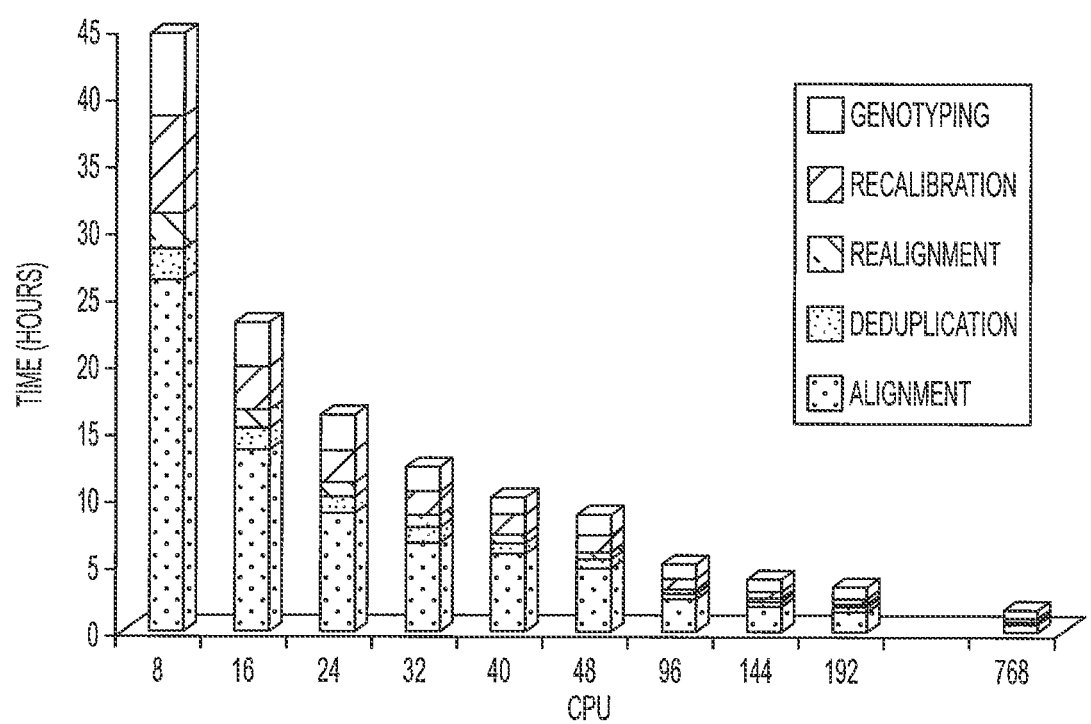
FIG. 11 is a chart showing performance of a current embodiment when increasing the number of processing cores from eight to 768.

By carefully exploring interdependencies among different sub-tasks, the pipeline achieved high parallelism and was able to complete data analysis in a fraction of the time. For instance, as shown in FIG. 11, a simple single-threaded implementation of the workflow took 10 days to process a whole human genome sample, while a parallel version, according to the above disclosure, using 748 cores, only required under 2 hours.

Figure 12:
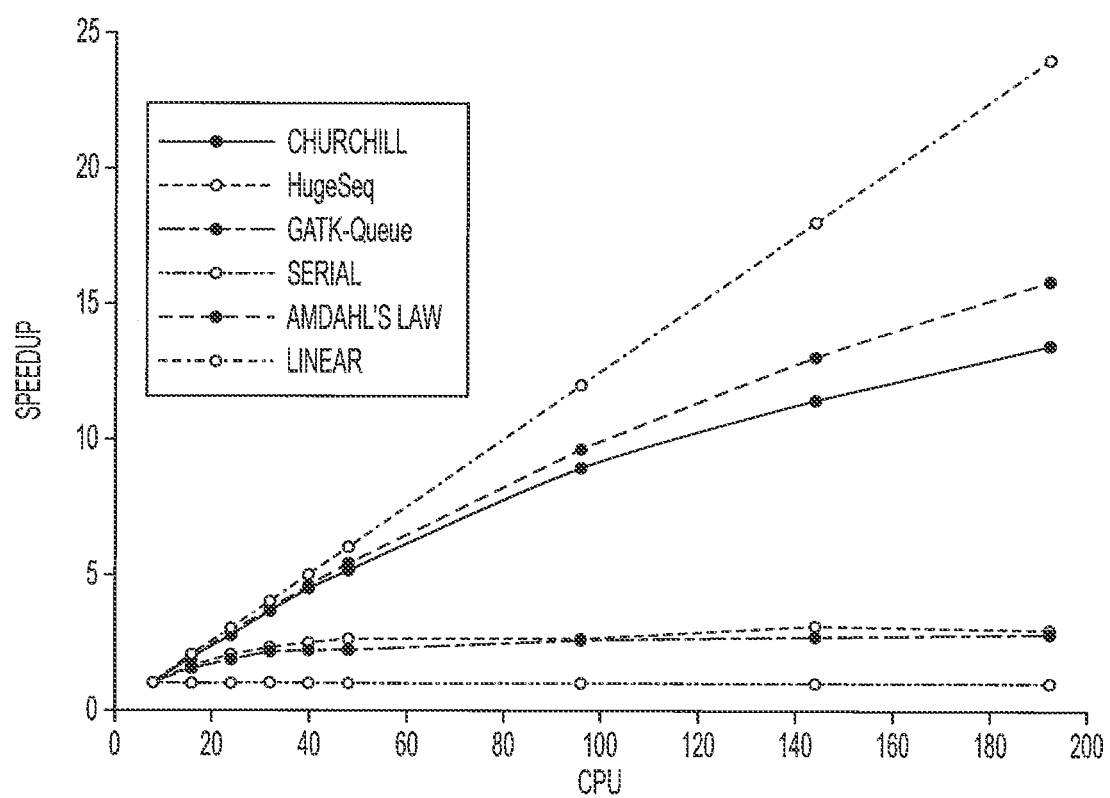
FIG. 12 is a linear chart comparison of an exemplary embodiment's performance versus alternative pipelines using increasing numbers of CPU cores.

The speedup of Churchill increases as more cores are utilized, enabling near-linear scalability of analysis workflow beyond 24 cores. FIG. 12 shows the scalability of Churchill vs. alternative pipelines using different number of cores; i.e., the fold speedup is plotted as a function of the cores used. For comparison purpose the linear speedup and that predicted by the Amdahl's law assuming a one-hour sequential time were also included (See, Rodgers, D. P. in Proceedings of the 12th annual international symposium on Computer architecture 225-231 (IEEE Computer Society Press, Boston, Mass., United States; 1985)). It is evident that Churchill's scalability closely matches that predicted by the Amdahl's law.

BRIEF CONCLUSIONS (a) The current disclosure provides systems and methods that accurately parallelize the read deduplication process through implementation of an artificial chromosome strategy. Read pairs with both mates mapped to different subregions are saved in a separate BAM file. These reads can then be processed separately, enabling appropriate parallelization of deduplication by subregion and drastically speeding up analysis time. The current parallelized deduplication returns identical results to the current, much slower, approach of merging all BAM files into a single file prior to deduplication.

(b) The current disclosure provides systems and methods that enable parallel processing of the subsequent realignment, recalibration and genotyping steps. Through utilization of an overlapping chromosomal subregion strategy, the current pipeline achieves unprecedented analytical processing time of these steps, without sacrificing data integrity.

(c) The current analysis is deterministic—regardless of the number of subregions used to parallelize the process, the final result is identical, making the current systems and methods an optimal solution for clinical applications. Other parallelization strategies fail to achieve this level of determinism or have to make sacrifices in data quality for speed.

While the systems and methods described herein constitute exemplary embodiments of the current disclosure, it is to be understood that the scope of the claims are not intended to be limited to the disclosed forms, and that changes may be made without departing from the scope of the claims as understood by those of ordinary skill in the art. Further, while objects and advantages of the current embodiments have been discussed, it is not necessary that any or all such objects or advantages be achieved to fall within the scope of the claims.

What is claimed is:

1. A method for improving the utilization of processing capability of a computing system analyzing genetic sequence data associated with a subject, the method comprising:

receiving, by the computer system, the genetic sequence data associated with the subject, the genetic sequence data specifying a plurality of chromosomes and mitochondrial DNA;

splitting the genetic sequence data into a plurality of subsets, each subset corresponding to either one chromosome of the plurality of chromosomes or the mitochondria DNA;

defining an inter-subset of the genetic sequence data for read pairs with both mates mapped to different subsets of the plurality of subsets; and analyzing the obtained genetic sequence data by the computer system by dividing one or more processing steps in the analysis among a plurality of parallel processing paths, each parallel processing path corresponding to a subset of the plurality of subsets, each parallel processing path corresponding to either a chromosome of the plurality of chromosomes or the mitochondrial DNA.

2. The method of claim 1, wherein the plurality of chromosomes includes twenty two autosomal chromosomes and two sex chromosomes.

3. The method of claim 1, wherein the subject is a human subject.

4. The method of claim 1, wherein the parallel processing paths further correspond to read pairs with both mates mapped to the same subset.

5. The method of claim 1, wherein the one or more processing steps includes local realignment.

6. The method of claim 1, wherein the one or more processing steps includes genotyping.

7. The method of claim 1, wherein the plurality of processing paths for the one or more processing steps does not include a path for processing the inter-subset.

8. The method of claim 1, wherein the one or more processing steps include marking duplicates.

9. The method of claim 4, wherein the plurality of processing paths includes at least twenty six parallel processing paths respectively corresponding to twenty two autosomal chromosomes, two sex chromosomes, one mitochondrial DNA, and one processing path corresponding to the inter-subset.

10. The method of claim 1, wherein the analyzing includes mapping reads to a reference genome, the mapping being divided into the plurality of parallel processing paths.

11. The method of claim 2, wherein the analyzing includes mapping reads to a reference genome, wherein the mapping reads to the reference genome is divided into the plurality of parallel processing paths.

12. The method of claim 1, wherein at least two subsets in the plurality of subsets include reads respectively mapped to the at least two subsets.

13. The method of claim 12, wherein the plurality of subsets and the inter-subset of the genetic data are each in the form of a separate binary alignment map (BAM) file of a set of BAM files in the respective parallel processing paths.

14. The method of claim 13, wherein the analyzing includes performing deduplication on the set of BAM files.

15. The method of claim 13, wherein the set of BAM files include a first plurality of BAM files corresponding to read pairs in which both mates are mapped to the same data set, and at least one BAM file corresponding to read pairs in which both mates are mapped to different data sets.

16. The method of claim 15, wherein each BAM file of the first plurality of BAM files is associated with a chromosome in which both mates are mapped to the same chromosome.

17. The method of claim 15, wherein the first plurality of BAM files correspond to one or more segments of chromosomes with both mates mapped to the respective segments of chromosomes in each BAM file.

18. The method of claim 17, wherein the total number of the set of BAM files corresponds to a number of processor cores respectively performing parallel processing operations.

19. The method of claim 1, wherein the processing a plurality of subsets of the genetic sequence data among the plurality of parallel processing paths includes a step of spawning multiple processes using the xargs utility in the Linux environment.

20. The method of claim 1, wherein the processing a plurality of subsets of the genetic sequence data among the plurality of parallel processing paths includes a step of utilizing GNU's Not Unix (GNU) parallel processing.

21. The method of claim 1, wherein the analyzing the genetic sequence data among the plurality of parallel processing paths is performed in a distributed cluster environment.

22. The method of claim 21, wherein the analyzing the genetic sequence data among the plurality of parallel processing paths includes submitting jobs to a job queue and managing the executions of the jobs by a job scheduler.

23. The method of claim 22, wherein the jobs are submitted in a manner so as to maintain task dependency.

24. The method of claim 23, wherein the jobs are synchronized to maintain task dependency.

25. The method of claim 24, wherein the jobs are submitted with dependency directions so as to maintain task dependency.

26. The method of claim 1, wherein the processing a plurality of subsets of the genetic sequence data among the plurality of parallel processing paths is performed utilizing distributed Make utilities.

27. The method of claim 26, wherein the distributed Make utility includes qmake in the Sun Grid Engine (SGE) environment.

28. The method of claim 26, wherein the distributed Make utility includes distmake in the Sun Grid Engine (SGE) or Portable Batch System (PBS) environment.

29. The method of claim 1, wherein the processing a plurality of subsets of the genetic sequence data among the plurality of parallel processing paths is performed utilizing a distributed file system.

30. The method of claim 29, wherein the distributed file system involves the MapReduce framework.

31. The method of claim 1, wherein the processing a plurality of subsets of the genetic sequence data among the plurality of parallel processing paths is performed utilizing a cloud computing environment.

32. The method of claim 1 wherein the method further comprises, prior to the analyzing step:
performing deduplication on the inter-subset to produce a deduplicated inter-subset; and
splitting the deduplicated inter-subset according to the respective plurality of subsets to produce a respective plurality of split deduplicated inter-subsets; and
merging the each of the split deduplicated inter-subsets with its corresponding subset in the plurality of subsets.

33. A method for improving utilization of processing capability of a computing system analyzing genetic sequence data of a subject, comprising:
obtaining, by the computer system, genetic sequence data associated with the subject; and
analyzing the obtained genetic sequence data by the computer system by mapping reads of the genetic sequence data to a reference genome using a plurality of parallel processing paths,
wherein a number of parallel processing paths of the plurality of parallel processing paths corresponds to a number of processor cores of the computing system.

34. The method of claim 33, wherein:
the analyzing includes a local realignment step
that is divided into a subset of parallel processing paths of the plurality of processing paths, the subset of parallel processing paths corresponding to selected chromosomes.

35. The method of claim 34, wherein the local realignment step is divided into twenty-five parallel processing paths of the plurality of parallel processing paths, the twenty-five parallel processing paths respectively corresponding to twenty two autosomal chromosomes of the genetic sequence data, two sex chromosomes of the genetic sequence data, and one mitochondrial DNA of the genetic sequence data.

36. The method of claim 33, wherein:
the analyzing including unified genotyper step
that is divided into a subset of parallel processing paths of the plurality of parallel processing paths respectively corresponding to twenty two autosomal chromosomes of the genetic sequence data, two sex chromosomes of the genetic sequence data, and one mitochondrial DNA of the genetic sequence data.

37. The method of claim 33, wherein the analyzing includes one or more steps divided into a subset of parallel processing paths of the plurality of parallel processing paths, each processing path of the subset of parallel processing paths respectively corresponding to a chromosome of the genetic sequence data.

38. The method of claim 33, wherein the analyzing includes one or more steps divided into a first set of parallel processing paths of the plurality of parallel processing paths, each parallel processing path of the first set of parallel processing paths associated with a read pair in which both mates are mapped to the same data set, and a second set of processing paths of the plurality of parallel processing paths, each parallel processing path of the second set of parallel processing paths associated with a read pair in which both mates are mapped to different data sets.

39. The method of claim 38, wherein the number of processor cores includes at least eight processor cores.

40. The method of claim 38, wherein each data set is associated with a segment of the genome sequence data.

41. The method of claim 40, wherein the subject is a human subject.

42. The method of claim 38, wherein the one or more steps are divided into the first set of parallel processing paths associated with read pairs in which both mates are mapped to the same data sets, and the second set of parallel processing paths associated with read pairs in which both mates are mapped to different data sets are taken from a group consisting of: duplicates removal, base quality score recalibration and variant quality score recalibration.

43. A method of improving scalability of a computer system analyzing genetic sequence data, comprising:
obtaining, by the computer system, genetic sequence data associated with a subject, the computer system including a plurality of processing cores;
splitting the genetic sequence data into a plurality of segments;
processing the genetic sequence data such that read pairs with both mates mapped to the same segment are saved to an intra-segmental binary alignment map (BAM) file associated with that segment to generate a plurality of intra-segmental BAM files;
processing the genetic sequence data such that read pairs with both mates mapped to different segments are saved into an inter-segmental BAM file;
processing the plurality of intra-segmental BAM files along a plurality of parallel processing paths, each processing path corresponding to a different processor core from a plurality of processing cores of the computer system.

44. The method of claim 43, further comprising removing duplicates on the inter-segmental BAM file to produce a dedpulicated inter-segmental BAM file.

45. The method of claim 44, further comprising merging reads from the deduplicated inter-segmental BAM file into the plurality of intra-segmental BAM files to produced a plurality of merged intra-segmental BAM files.

46. The method of claim 45, further comprising, following the merging step, processing the plurality of merged intra-segmental BAM files along additional parallel processing paths.

47. The method of claim 46, wherein the one or more of the following processes are processed along the additional parallel processing paths: realignment, analyzing covariation, recalibrating quality scores, and genotyping.

48. A method of improving scalability of a computer system analyzing genetic sequence data, comprising:
(a) obtaining, by the computer system, genetic sequence data associated with a subject;
(b) splitting the genetic sequence data into a plurality of segments, a number of segments of the plurality of segments based on the size of the genetic sequence data and a number of available processing cores of the computer system;
(c) processing the genetic sequence data such that intra-segment reads with read pairs with both mates mapped to the same data set, are saved to a respective binary alignment map (BAM) file from a plurality of BAM files associated with that respective segment;
(d) processing the genetic sequence data such that inter-segment reads with read pairs with both mates mapped to different segments, are saved into an inter-segment BAM file; and
(e) processing a first set of BAM files of the plurality of BAM files along a plurality of parallel processing paths.

49. The method of claim 48, further comprising the steps of:
performing a de-duplication process on the inter-segment BAM file to produce a set of deduplicated inter-segment reads;
merging each deduplicated inter-segment read from the set of deduplicated inter-segment reads back into a respective BAM file from the plurality of BAM files associated with a segment from which the inter-segment read was obtained.

50. The method of claim 49, wherein the processing step (e) includes a step of local realignment on each of the first sets of BAM files.

51. The method of claim 49, wherein the processing step (e) includes a step of duplicate read removal on each of the first sets of BAM files.

52. The method of claim 49, wherein the processing step (e) includes a step of base quality score recalibration on each of the first set of BAM files.

53. The method of claim 49, wherein the processing step (e) includes a step of variant calling for each BAM file from the first set of BAM files.

54. The method of claim 48, wherein the processing step (e) includes a step of local realignment on each of the first sets of BAM files.

55. The method of claim 48, wherein the processing step (e) includes a step of duplicate read removal on each of the first sets of BAM files.

56. The method of claim 48, wherein the processing step (e) includes a step of base quality score recalibration on each of the first sets of BAM files.

57. The method of claim 48, wherein the processing step (e) includes a step of variant calling for each BAM file from the first set of BAM files.

58. The method of claim 48, wherein the number of segments in the splitting step (b) is greater than the number of human chromosomes.

59. The method of claim 48, wherein the segments in the splitting step (b) are of the same size.

60. The method of claim 48, wherein the plurality of segments includes a segment associated with a first chromosomal sub-region and a segment associated with a second chromosomal sub-region.

* * * * *